(12) United States Patent
Konishi et al.

(10) Patent No.: US 9,782,218 B2
(45) Date of Patent: Oct. 10, 2017

(54) THERMOCOAGULATION/CUTTING DEVICE

(71) Applicant: OLYMPUS CORPORATION, Hachioji-shi, Tokyo (JP)

(72) Inventors: Sumihito Konishi, Akishima (JP); Tsuyoshi Hayashida, Hachioji (JP); Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/154,592

(22) Filed: May 13, 2016

(65) Prior Publication Data

US 2016/0249975 A1   Sep. 1, 2016

Related U.S. Application Data

(63) Continuation of application No. PCT/JP2014/083009, filed on Dec. 12, 2014.

(30) Foreign Application Priority Data

Dec. 20, 2013   (JP) ................................. 2013-264673

(51) Int. Cl.
*A61B 18/14*   (2006.01)
*A61B 18/00*   (2006.01)

(52) U.S. Cl.
CPC *A61B 18/1445* (2013.01); *A61B 2018/00607* (2013.01)

(58) Field of Classification Search
None
See application file for complete search history.

(56) References Cited

U.S. PATENT DOCUMENTS

| 2006/0217709 A1* | 9/2006 | Couture | A61B 18/1442 606/51 |
| 2008/0183251 A1* | 7/2008 | Azar | A61B 18/18 607/101 |

(Continued)

FOREIGN PATENT DOCUMENTS

| JP | S54-82488 U | 6/1979 |
| JP | 3152932 B2 | 4/2001 |

(Continued)

OTHER PUBLICATIONS

Mar. 17, 2015 Search Report issued in International Patent Application No. PCT/JP2014/083009.

(Continued)

*Primary Examiner* — Joseph Stoklosa
*Assistant Examiner* — Nicole L Pobre
(74) *Attorney, Agent, or Firm* — Oliff PLC

(57) ABSTRACT

A thermocoagulation/cutting device 11 includes an exothermic part 13 made of a meta; a first current supply portion 41 projecting integrally from the exothermic part 13; a second current supply portion 42 projecting integrally from the exothermic part 13; and a third current supply portion 43 projecting integrally from the exothermic part 13. The thermocoagulation/cutting device 11 includes a controller 16. The controller 16 is capable of causing an electric current to flow between the first current supply portion 41 and second current supply portion 42, between the first current supply portion 41 and third current supply portion 43, or between the second current supply portion 42 and third current supply portion 43.

8 Claims, 10 Drawing Sheets

(56) References Cited

U.S. PATENT DOCUMENTS

2011/0306973 A1* 12/2011 Cummings ........ A61B 18/1445
606/48
2014/0276754 A1* 9/2014 Gilbert .................. A61B 18/18
606/33

FOREIGN PATENT DOCUMENTS

| JP | 2002-136525 A | 5/2002 |
| JP | 4762149 B2 | 8/2011 |
| JP | 2012-249807 A | 12/2012 |
| WO | 2012/133512 A1 | 10/2012 |

OTHER PUBLICATIONS

Jun. 30, 2016 International Preliminary Report on Patentability issued in PCT/JP2014/083009.

* cited by examiner

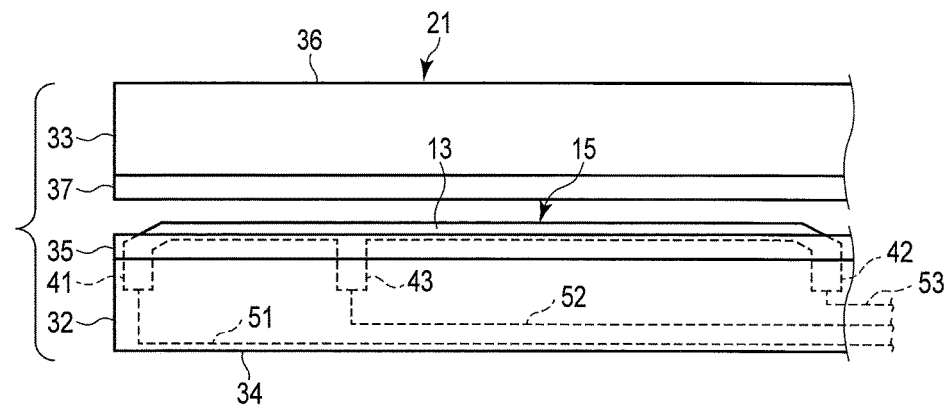
F I G. 4
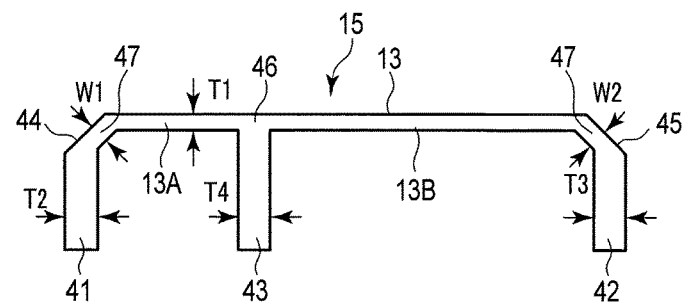
F I G. 5
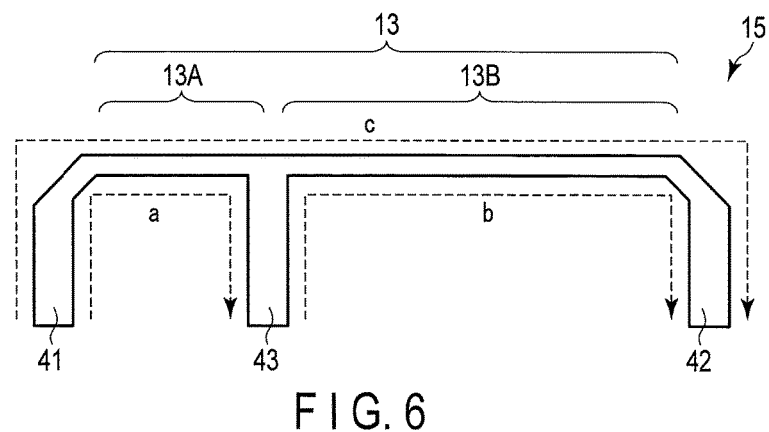
F I G. 6

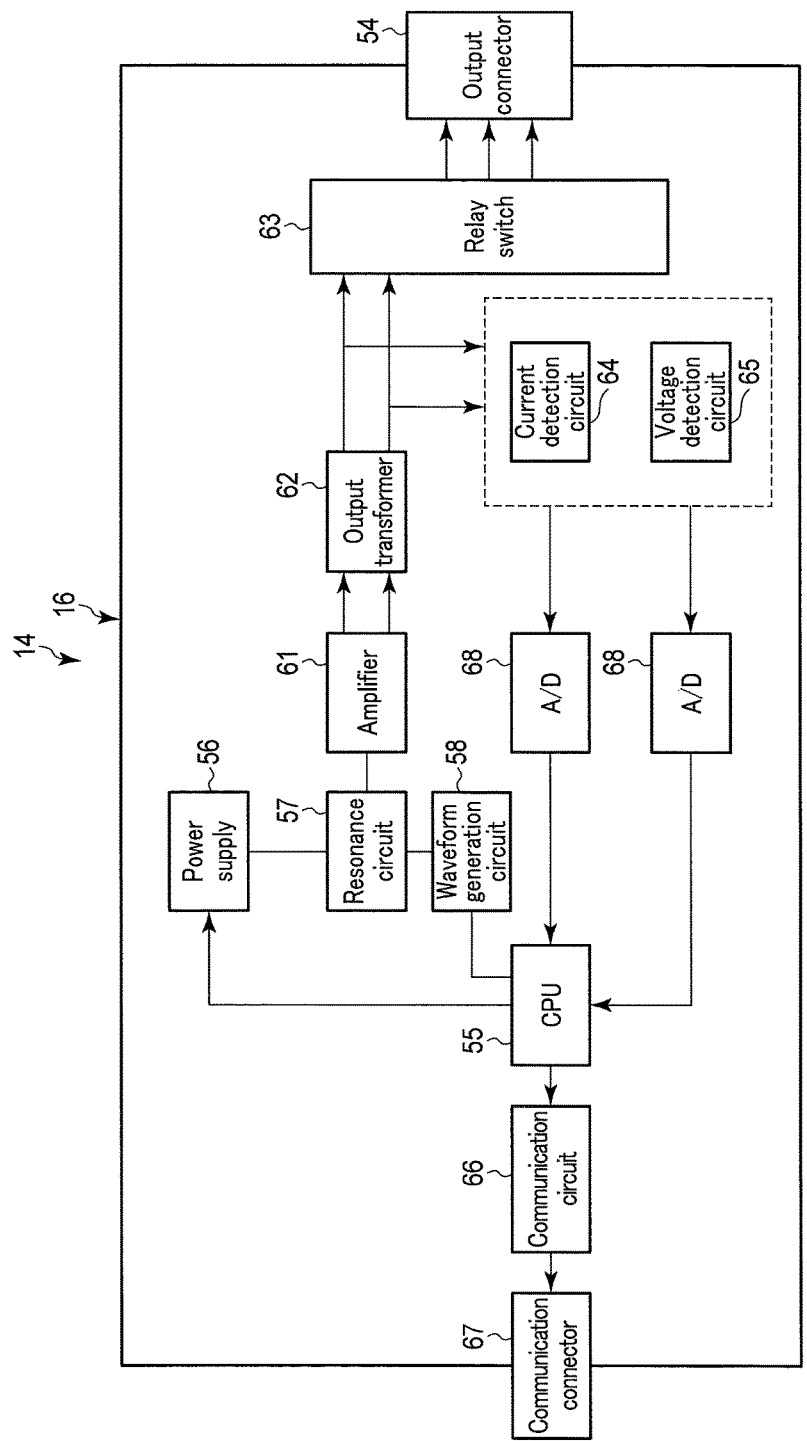
F I G. 7

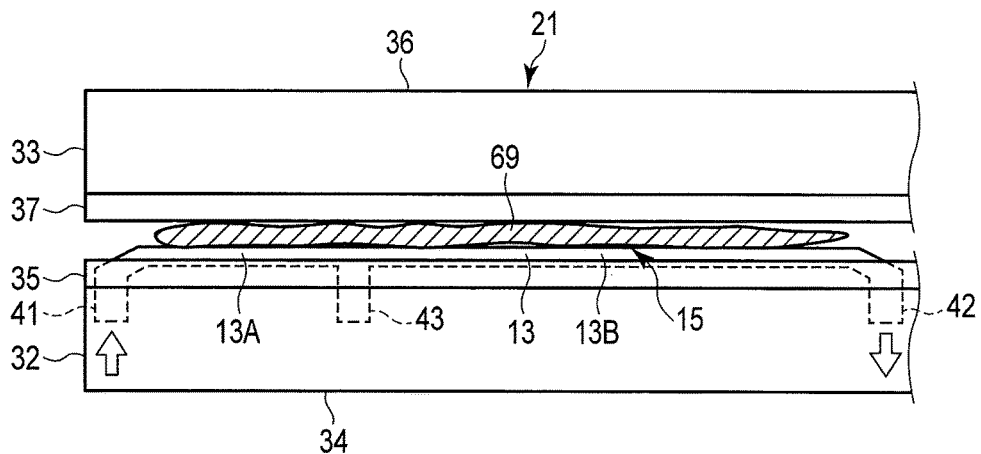
F I G. 10
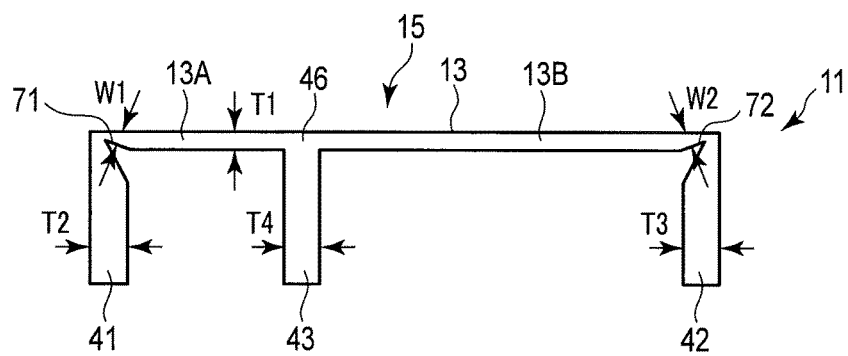
F I G. 11
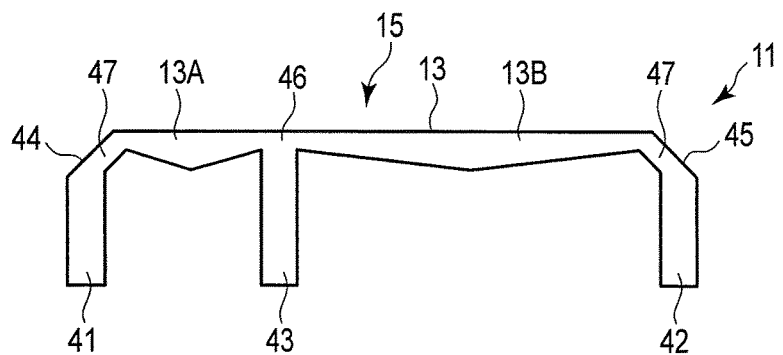
F I G. 12

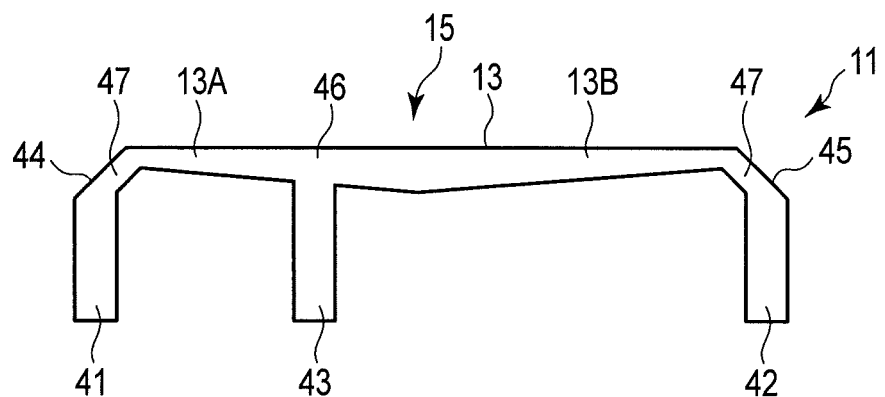
F I G. 13
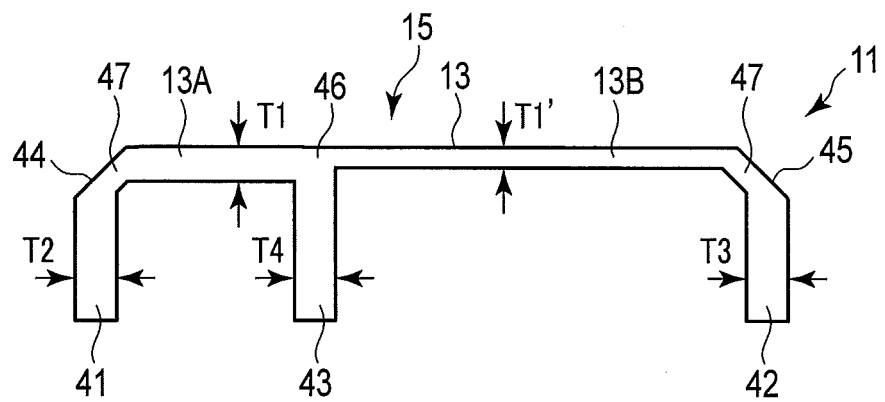
F I G. 14

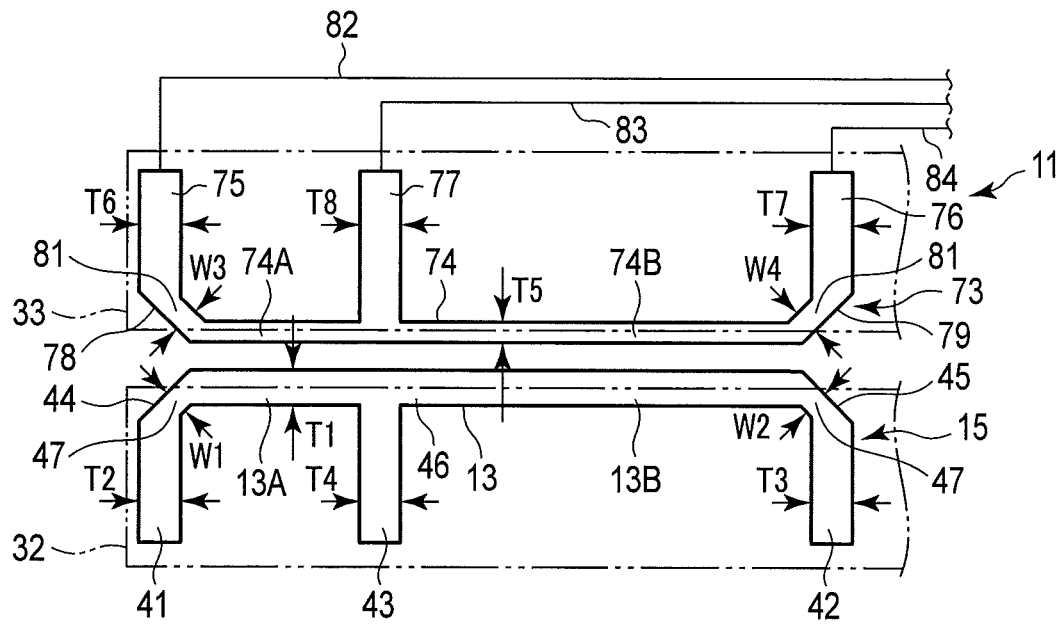
F I G. 15
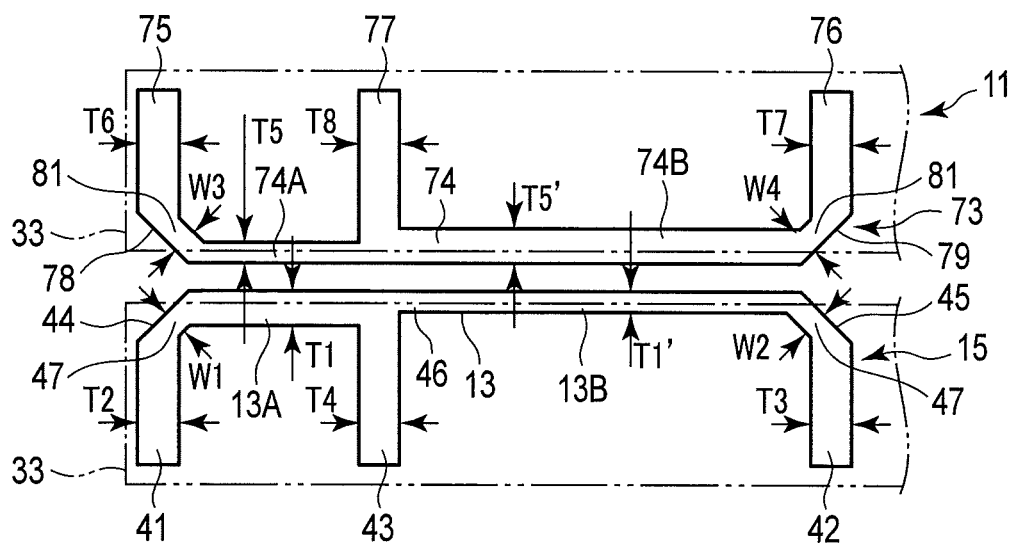
F I G. 16

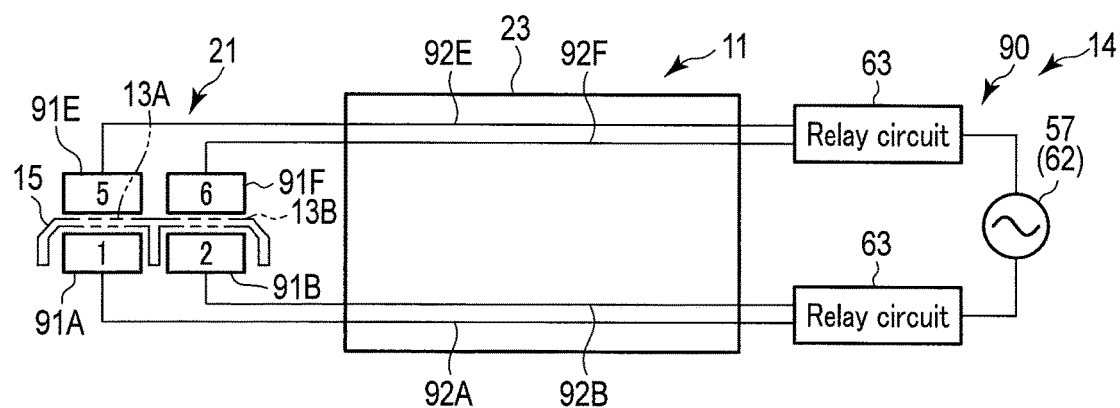
F I G. 20

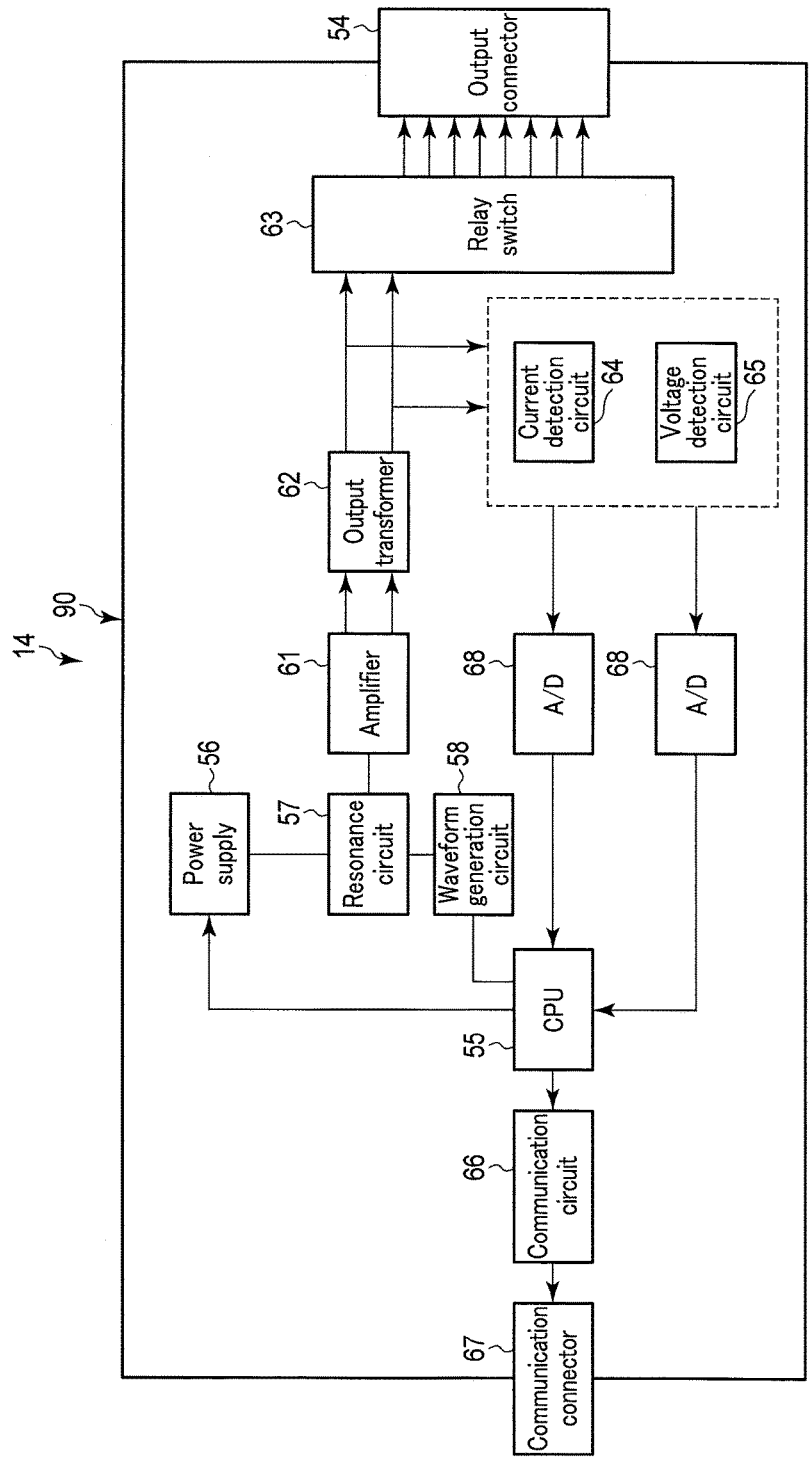
F I G. 21

THERMOCOAGULATION/CUTTING DEVICE

CROSS-REFERENCE TO RELATED APPLICATIONS

This application is a Continuation Application of PCT Application No. PCT/JP2014/083009, filed Dec. 12, 2014 and based upon and claiming the benefit of priority from prior Japanese Patent Application No. 2013-264673, filed Dec. 20, 2013, the entire contents of all of which are incorporated herein by reference.

BACKGROUND OF THE INVENTION

1. Field of the Invention

The present invention relates to a thermocoagulation/cutting device which performs coagulation and cutting by applying heat energy to a living body tissue.

2. Description of the Related Art

Japanese Patent No. 4762149 (patent document 1) discloses a cautery of a so-called direct exothermic type, in which a part that comes in contact with a living body tissue directly produces heat. In this cautery, a resistance heating element (heater wire) is disposed on a grasping surface.

Japanese Patent No. 3152932 (patent document 2) discloses an electrothermal surgical blade of a so-called indirect exothermic type, in which a heating element is provided adjacent to an outer layer which applies heat to a living body tissue. In this electrothermal surgical blade, the heat produced by the heating element is transferred to the outer layer and both side cut faces.

Jpn. Pat. Appln. KOKAI Publication No. 2012-249807 (patent document 3) discloses a therapeutic treatment device. In this document, an exothermic chip driving circuit supplies under, the control of a controller, electric power to resistance patterns of exothermic chips via exothermic chip power lines in order to produce heat. The exothermic chip driving circuit can individually vary power amounts which are supplied to the respective exothermic chips.

BRIEF SUMMARY OF THE INVENTION

In order to achieve the above object, a thermocoagulation/cutting device according to one mode of the present invention includes a rod-shaped grasping section; an exothermic part made of a metal and provided on a surface of the grasping section linearly along a longitudinal direction of the grasping section; a first current supply portion projecting integrally from the exothermic part on a distal end side of the grasping section; a second current supply portion projecting integrally from the exothermic part on a proximal end side of the grasping section; and a third current supply portion projecting integrally from the exothermic part at a position between the first current supply portion and second current supply portion. The thermocoagulation/cutting device includes a controller. The controller is electrically connected to the first current supply portion, second current supply portion and third current supply portion. The controller is capable of causing an electric current to flow, in the exothermic part, between the first current supply portion and second current supply portion, between the first current supply portion and third current supply portion, or between the second current supply portion and third current supply portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic view illustrating, from a side surface direction, the coagulation/cutting unit shown in FIG. 2.

FIG. 5 is a side view illustrating, from the side surface direction, a thermal blade of the coagulation/cutting unit shown in FIG. 4.

FIG. 6 is a schematic view illustrating paths of an electric current flowing in the thermal blade shown in FIG. 5.

FIG. 7 is a block diagram illustrating a controller of a power supply device of the thermocoagulation/cutting device shown in FIG. 1.

FIG. 10 is a side view illustrating a state in which a living body tissue is clamped by the entirety of the coagulation/cutting unit shown in FIG. 4.

FIG. 11 is a side view illustrating a thermal blade of a thermocoagulation/cutting device of a second embodiment.

FIG. 12 is a side view illustrating a thermal blade of a thermocoagulation/cutting device of a third embodiment.

FIG. 13 is a side view illustrating a modification of the thermal blade of the thermocoagulation/cutting device of the third embodiment.

FIG. 14 is a side view illustrating a thermal blade of a thermocoagulation/cutting device of a fourth embodiment.

FIG. 15 is a schematic view illustrating, from the side surface direction, a coagulation/cutting unit of a thermocoagulation/cutting device of a fifth embodiment.

FIG. 16 is a schematic view illustrating, from the side surface direction, a modification of the coagulation/cutting unit of the thermocoagulation/cutting device of the fifth embodiment.

FIG. 20 is a schematic view illustrating the entire structure of a thermocoagulation/cutting device of an seventh embodiment.

FIG. 21 is a block diagram illustrating a second controller of a power supply device of the thermocoagulation/cutting device shown in FIG. 20.

DESCRIPTION OF EMBODIMENTS

[First Embodiment]

Figure 1:
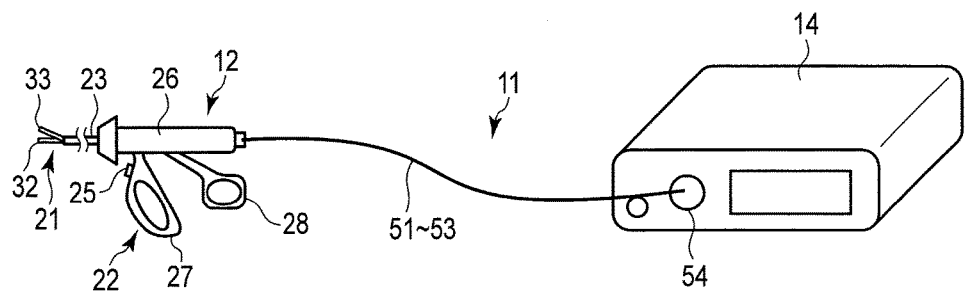
FIG. 1 is a schematic view illustrating the entire structure of a thermocoagulation/cutting device of a first embodiment.

The present invention relates to a surgical operation device which includes a first jaw (grasping section) and a second jaw (second grasping section) which is engageable with this grasping section, and applies heat energy to a living body tissue which is grasped therebetween, thereby performing treatment such as cutting or coagulation. FIG. 1 schematically illustrates the structure of the entirety of a thermocoagulation/cutting device of the present embodiment.

A thermocoagulation/cutting device 11 includes a handpiece 12; a power supply device 14 which supplies an electric current to an exothermic part 13 of the handpiece 12; and a cable accommodating therein a plurality of current supply lines 51 to 53 which connect the handpiece 12 and power supply device 14. The power supply device 14 includes a controller 16 (see FIG. 7) for controlling a thermal blade 15 of the handpiece 12.

Figure 2:
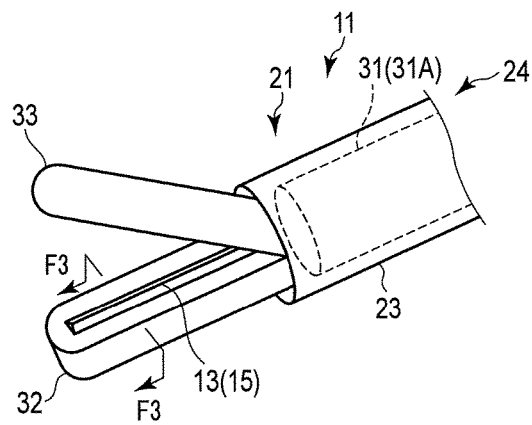
FIG. 2 is a perspective view illustrating a coagulation/cutting unit of the thermocoagulation/cutting device shown in FIG. 1.

As illustrated in FIG. 1 and FIG. 2, the handpiece 12 includes a coagulation/cutting unit 21 (coagulation/cutting section) which is openable/closable like scissors; a handle unit 22 (operation section) which a doctor holds and operates in order to open/close the coagulation/cutting unit 21; a cylindrical sheath section 23 which couples the coagulation/cutting unit 21 and handle unit 22; an operational force transmission mechanism 24 which is partly positioned inside the sheath section 23 and transmits an operational force of the handle unit 22 to the coagulation/cutting unit 21; and a switch 25 provided on the handle unit 22.

The handle unit 22 includes a cylindrical portion 26 which is connected to the sheath section 23; a stationary handle 27 which is provided stationary relative to the cylindrical portion 26; and a movable handle 28 which is rotatable relative to the cylindrical portion 26 and stationary handle 27. The operational force transmission mechanism 24 includes a transmission member 31 (driving pipe) which is provided to be movable in an axial direction of the sheath section 23 in the inside of the sheath section 23; and a spring member which is interposed between the transmission member 31 and movable handle 28. By rotating the movable handle 28 in a direction away from the stationary handle 27, a user (doctor) can rotate a second jaw 33 in a manner to move away from a first jaw 32 in the coagulation/cutting unit 21. Similarly, if the user rotates the movable handle 28 in such a direction as to approach the stationary handle 27, the user can rotate the second jaw 33 in a manner to engage with (mesh with) the first jaw 32 in the coagulation/cutting unit 21. The spring member applies a repulsive force in such a direction that the movable handle 28 moves away from the stationary handle 27. Thus, when the user rotates the movable handle 28 relative to the stationary handle 27 and clamps a living body tissue between the first jaw 32 and second jaw 33, the user can feel a slight resistance.

An insulation tube 31A, which is formed of an insulating material, is provided on an inner peripheral side of the transmission member 31 (driving pipe).

The switch 25 can advance/retreat between an initial position, and a position where the switch 25 is pushed from the initial position toward the inner side of the stationary handle. To be more specific, the switch 25 can advance/retreat among a first pushed-in position where the switch 25 is pushed in from the initial position by ⅓ of the entire stroke thereof, a second pushed-in position where the switch 25 is pushed in from the initial position by ⅔ of the entire stroke, and a third pushed-in position where the switch 25 is pushed in from the initial position by the entire stroke.

Figure 3:
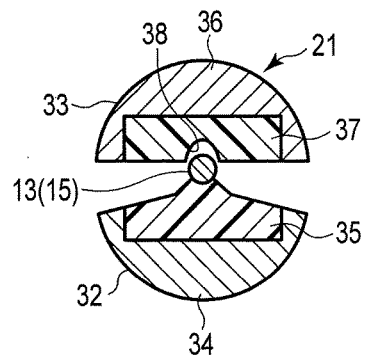
FIG. 3 is a cross-sectional view of the coagulation/cutting unit shown in FIG. 2, FIG. 3 being taken along line F3-F3 in FIG. 2.

The coagulation/cutting unit 21 includes the first jaw 32 (grasping section) which is provided stationary relative to the sheath section 23, the second jaw 33 (second grasping section) which is provided rotatable relative to the first jaw 32 and sheath section 23, and the thermal blade 15 which is made of a metal and is provided on a surface of the first jaw 32. The thermal blade 15 may be provided on the second jaw 33 (second grasping section) side. As illustrated in FIG. 3, the first jaw 32 is provided, for example, in a rod shape with a semicircular cross section. The first jaw 32 includes a first jaw body 34 which is made of a metal and forms the contour of the first jaw 32, and a first insulation member 35 which is positioned inside the first jaw body 34. The exothermic part 13 of the thermal blade 15 is fixed on a raised portion of the first insulation member 35.

As illustrated in FIG. 2 and FIG. 3, the second jaw 33 is provided, for example, in a rod shape with a semicircular cross section. The second jaw 33 is supported by a pin which is fixed to a distal end portion of the sheath section 23, and is attached to be rotatable about the pin. Thus, the second jaw 33 can be engaged with the first jaw 32, and can be separated from the first jaw 32. The second jaw 33 includes a second jaw body 36 which is made of a metal and forms the contour of the second jaw 33, and a second insulation member 37 which is positioned inside the second jaw body 36. The second insulation member 37 is provided with a groove portion 38 in which the thermal blade 15 is fitted when the first jaw 32 and second jaw 33 are engaged. The groove portion 38 is recessed along the shape of the thermal blade 15, and extends in the longitudinal direction of the second jaw 33.

As illustrated in FIG. 4 and FIG. 5, the thermal blade 15 is integrally formed of a metallic material, for example, in a substantially "E" shape. The thermal blade 15 is formed, for example, by press working by punching a substantially "E" shaped piece out of a single metal plate.

The thermal blade 15 includes the exothermic part 13 which is linearly provided along the longitudinal direction of the first jaw 32 (grasping section); a first current supply portion 41 provided on a distal end side of the first jaw 32; a second current supply portion 42 which is provided on a proximal end side opposite to the distal end side of the first jaw 32; and a third current supply portion 43 which projects from the exothermic part 13 at a position between the first current supply portion 41 and second current supply portion 42. The exothermic part 13 includes a first portion 13A provided between the first current supply portion 41 and third current supply portion 43, and a second portion 13B provided between the second current supply portion 42 and third current supply portion 43.

Each of the first current supply portion 41 to third current supply portion 43 is formed integral with the exothermic part 13, and projects, for example, from the exothermic part 13 in a direction crossing (perpendicular to) a direction of extension of the exothermic part 13. In other words, each of the first current supply portion 41 to third current supply portion 43 projects integrally from the exothermic part 13.

The third current supply portion 43 is located more on the distal end side of the first jaw 32 than a middle position of the exothermic part 13 in the longitudinal direction of the first jaw 32.

The thermal blade 15 includes a first chamfered portion 44 on an outside of a corner portion formed by the exothermic part 13 and first current supply portion 41 (a portion at which the exothermic part 13 and first current supply portion 41 intersect). The thermal blade 15 includes a second chamfered portion 45 on an outside of a corner portion formed by the exothermic part 13 and second current supply portion 42 (a portion at which the exothermic part 13 and second current supply portion 42 intersect).

Specifically, the exothermic part 13 includes an exothermic part body 46, and gradient portions 47 provided at both end portions in the longitudinal direction of the exothermic part body 46. The gradient portions 47 are inclined to the exothermic part body 46 and first current supply portion 41 (or second current supply portion 42).

As illustrated in FIG. 5, a dimension T1 of the exothermic part 13 with respect to a direction crossing the longitudinal direction of the exothermic part 13 is less than, for example, a dimension T2 of the first current supply portion 41 in a direction crossing the longitudinal direction of the first current supply portion 41, a dimension T3 of the second current supply portion 42 in a direction crossing the longitudinal direction of the second current supply portion 42, and a dimension T4 of the third current supply portion 43 in a direction crossing the longitudinal direction of the third current supply portion 43. In short, in this embodiment, T1<T2=T3=T4. Thus, the resistance values of the first current supply portion 41 to third current supply portion 43 are lower than the resistance value of the exothermic part 13, and useless heat production of the first to third current supply portions 41 to 43 can be prevented.

A width W1 of the portion at which the exothermic part 13 and first current supply portion 41 intersect is less than a width T2 of the other portion of the first current supply portion 41. A width W2 of the portion at which the exothermic part 13 and second current supply portion 42 intersect is less than a width T3 of the other portion of the second current supply portion 42.

As illustrated in FIG. 4, the exothermic part 13 of the thermal blade 15 is exposed to the outside. The first current supply portion 41, second current supply portion 42 and third current supply portion 43 of the thermal blade 15 are inserted in through-holes which are provided in the first insulation member 35. The first current supply portion 41 is, at a distal end portion thereof, connected to the first current supply line 51. The second current supply portion 42 is, at a distal end portion thereof, connected to the second current supply line 52. The third current supply portion 43 is, at a distal end portion thereof, connected to the third current supply line 53.

The first current supply line 51 to the third current supply line 53 extend through a gap between the first jaw body 34 and first insulation member 35, and are connected to an output connector 54 of the controller 16 of the power supply device 14 through the inside of the sheath section 23 (insulation tube 31A) and the inside of the cylindrical portion 26 of the handle unit 22.

Next, referring to FIG. 7, a description is given of the structure of the controller 16 of the power supply device 14 of the thermocoagulation/cutting device 11 of the embodiment.

The controller 16 of the power supply device 14 includes a CPU 55, a power supply circuit 56, a resonance circuit 57, a waveform generation circuit 58, an amplifier 61, an output transformer 62, a relay switching circuit 63, the output connector 54, a current detection circuit 64, a voltage detection circuit 65, a communication circuit 66, and a communication connector 67.

The waveform generation circuit 58 generates a sine wave and a burst wave. A signal of the sine wave or burst wave, which is output from the waveform generation circuit 58, is input to the amplifier circuit 61 via the resonance circuit 57. The signal amplified by the amplifier 61 is applied to a primary winding side of the output transformer 62, and a high-frequency signal, which is a high-frequency output for the thermal blade 15, occurs on a secondary winding side of the output transformer 62.

The secondary winding of the output transformer 62 is connected to the output connector 54 which is integrated into, for example, a single unit, via the relay switching circuit 63 which switches a high-frequency signal that is output. The first to third current supply lines 51 to 53 are connected to the output connector 54. The relay switching circuit 63 of the controller 16 can select two current supply lines from the first to third current supply lines 51 to 53, and can cause a high-frequency current to flow through them.

In addition, the resonance circuit 57 is supplied with a power supply voltage from the power supply circuit 56 which is capable of varying a voltage, and the waveform generation circuit 58 and power supply circuit 56 are controlled by a central processing unit (hereinafter referred to as CPU 55). The CPU 55 controls the waveform generation circuit 58 and power supply circuit 56 in accordance with the setting of an output mode, an output set value, etc. In the meantime, at least two modes, namely a mode suited to coagulation of a living body tissue and a mode suited to cutting of a living body tissue, exist for the high-frequency signal which is output on the above-described secondary winding side. The output signal of the secondary winding of the output transformer 62 is input to the voltage detection circuit 65 and current detection circuit 64, which constitute a detection unit.

The voltage detection circuit 65 and current detection circuit 64 detect, that is, measure, the voltage and current of the high-frequency signal which is output from the secondary winding of the output transformer 62. The detected voltage and current are converted to a digital voltage signal and a digital current signal by analog-to-digital converters 68 (hereinafter referred to as A/D converters), respectively, and the digital voltage signal and current signal are input to the CPU 55.

Based on the input voltage signal and current signal, the CPU 55 detects, that is, calculates, high-frequency power of the product of them. In addition, the CPU 55 controls the power supply voltage of the power supply circuit 56 so that the value of the detected high-frequency power may become a set value which was set in advance.

Furthermore, the CPU 55 is connected to the communication connector 67 via the communication circuit which executes communication. The controller 16 is connected to an electric scalpel (not shown) or the like via the communication connector 67.

Figure 8:
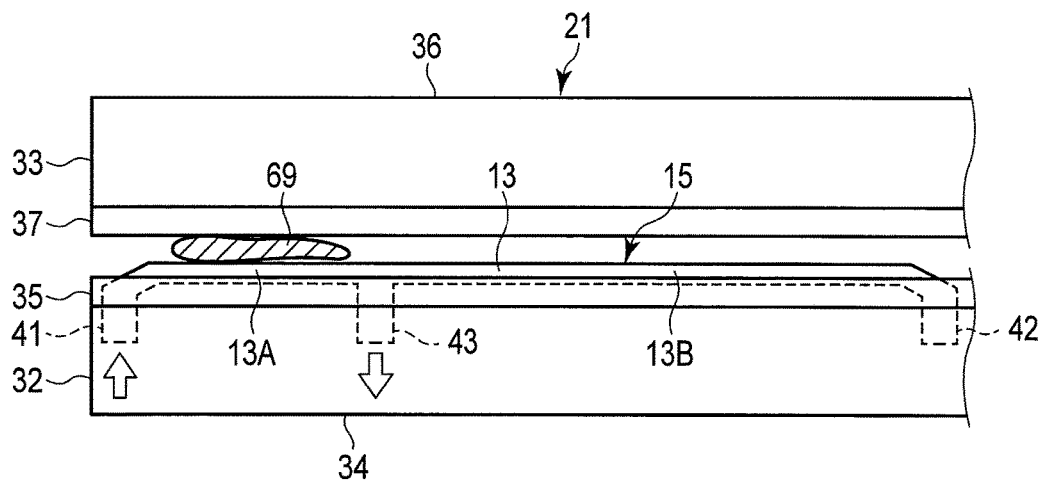
FIG. 8 is a side view illustrating a state in which a living body tissue is clamped on a distal end side of the coagulation/cutting unit shown in FIG. 4.
Figure 9:
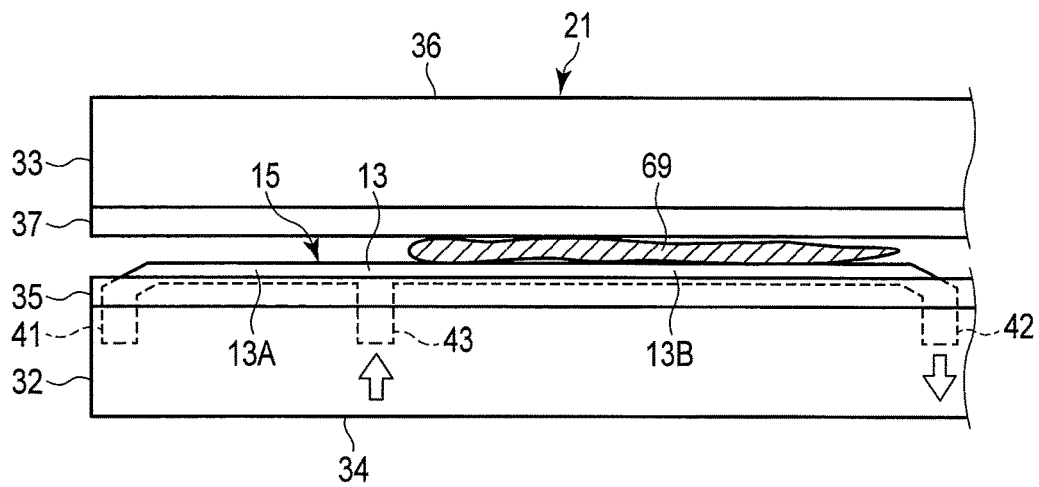
FIG. 9 is a side view illustrating a state in which a living body tissue is clamped on a proximal end side of the coagulation/cutting unit shown in FIG. 4.

Referring to FIG. 8 to FIG. 10, a concrete heat production control of the thermal blade 15 is described. In the present embodiment, it is possible to select, by the judgement of the user, which portion of the thermal blade 15 is caused to produce heat. As illustrated in FIG. 6, for example, when a distal end portion of the thermal blade 15, which corresponds to the distal end side of the first jaw 32, is to be caused to produce heat, an electric current is supplied via a path a from the first current supply portion 41 and third current supply portion 43, and the first portion 13A of the exothermic part 13 is caused to produce heat. When a proximal end portion of the thermal blade 15, which corresponds to the proximal end side opposite to the distal end side of the first jaw 32, is to be caused to produce heat, an electric current is supplied via a path b from the second current supply portion 42 and third current supply portion 43, and the second portion 13B of the exothermic part 13 is caused to produce heat. When the entirety of the thermal blade 15 is to be caused to produce heat, an electric current is supplied via a path c from the first current supply portion 41 and second current supply portion 42, and the entirety of the exothermic part 13 is caused to produce heat.

If a high-frequency current of the cutting mode is caused to flow to the thermal blade 15 via the first current supply line 51 to third current supply line 53, the temperature of the thermal blade 15 rises to, for example, 200° C. to 400° C., by the resistance in the inside of the thermal blade 15. It is more preferable that the temperature of the thermal blade 15 in the cutting mode is, for example, 250° C. to 400° C. If a high-frequency current of the coagulation mode is caused to flow to the thermal blade 15, the temperature of the thermal blade 15 rises to, for example, 60° C. to 150° C., by the resistance in the inside of the thermal blade 15. It is more preferable that the temperature of the thermal blade 15 in the coagulation mode is, for example, 100° C. to 150° C.

As illustrated in FIG. 8, for example, when a living body tissue is clamped on the distal end side of the first jaw 32 and second jaw 33, the user pushes the switch 25 of the handle unit 22 to the first pushed-in position. Thereby, an electric current is caused to flow between the first current supply portion 41 and third current supply portion 43, and the first portion 13A of the exothermic part 13 produces heat. By the first portion 13A which produces heat, treatment such as coagulation or cutting can be performed on a living body tissue 69.

As illustrated in FIG. 9, for example, when a living body tissue is clamped on the proximal end side opposite to the distal end side of the first jaw 32 and second jaw 33, the user pushes the switch 25 of the handle unit 22 to the second pushed-in position. Thereby, an electric current is caused to flow between the second current supply portion 42 and third current supply portion 43, and the second portion 13B of the exothermic part 13 produces heat. By the second portion 13B which produces heat, treatment such as coagulation or cutting can be performed on the living body tissue 69.

As illustrated in FIG. 10, for example, when a living body tissue is clamped by the entirety of the first jaw 32 and second jaw 33, the user pushes the switch 25 of the handle unit 22 to the third pushed-in position. Thereby, an electric current is caused to flow between the first current supply portion 41 and second current supply portion 42, and the entirety of the exothermic part 13 produces heat. By the entirety of the exothermic part 13 which produces heat, treatment such as coagulation or cutting can be performed on the living body tissue 69.

According to the first embodiment, the thermocoagulation/cutting device 11 includes the rod-shaped grasping section; the exothermic part 13 which is made of a metal and is provided on the surface of the grasping section linearly along the longitudinal direction of the grasping section; the first current supply portion 41 projecting integrally from the exothermic part 13 on the distal end side of the grasping section; the second current supply portion 42 projecting integrally from the exothermic part 13 on the proximal end side of the grasping section; the third current supply portion 43 projecting integrally from the exothermic part 13 at a position between the first current supply portion 41 and second current supply portion 42; and the controller 16 which is connected to the first current supply portion 41, second current supply portion 42 and third current supply portion 43 and is capable of causing an electric current to flow between the first current supply portion 41 and second current supply portion 42, between the first current supply portion 41 and third current supply portion 43, or between the second current supply portion 42 and third current supply portion 43.

According to the above-described structure, the exothermic part 13 can be caused to produce heat selectively between the first current supply portion 41 and second current supply portion 42, between the first current supply portion 41 and third current supply portion 43, or between the second current supply portion 42 and third current supply portion 43. Thereby, that portion of the exothermic part 13, which actually grasps the living body tissue 69, can properly be caused to produce heat, and heat can be transferred to the treatment part of the living body tissue 69 in a pinpoint manner. Accordingly, the exothermic part 13 directly produces heat, and the time that is needed for coagulation or cutting of the living body tissue 69 can be shortened, compared to a thermocoagulation/cutting device in which heat from an exothermic element is indirectly transferred via a heat transfer plate or the like. Thereby, a thermal effect (burn) on an internal organ existing near the treatment part can be reduced as much as possible.

In addition, the heat production of that portion of the exothermic part 13, which does not grasp the living body tissue 69, can be suppressed. Therefore, the volume of the exothermic part 13, which actually produces heat, can be decreased, the rise in temperature of the outside of the grasping section can be suppressed, and the thermal effect on an internal organ existing near the treatment part can be decreased.

Furthermore, when a tissue is cut by only the distal end side of the grasping section, the distal end side alone of the exothermic part 13 can be caused to produce heat. Besides, when cutting is not to be performed on the distal end side, such as when a large area of a membranous tissue including a blood vessel is grasped and cut, the proximal end side alone of the exothermic part 13 can be caused to produce heat.

According to the present embodiment, the width W1 of the portion at which the exothermic part 13 and first current supply portion 41 intersect is less than the width T2 of the other portion of the first current supply portion 41, and the width W2 of the portion at which the exothermic part 13 and second current supply portion 42 intersect is less than T3 of the other portion of the second current supply portion 42. In usual cases, since the portion at which the exothermic part 13 and first current supply portion 41 intersect and the portion at which the exothermic part 13 and second current supply portion 42 intersect constitute corner portions, these portions tend to have greater widths than the other portions. According to the above-described structure, an increase in width can be prevented at the portion at which the exothermic part 13 and first current supply portion 41 intersect and the portion at which the exothermic part 13 and second current supply portion 42 intersect, and the resistance values of these portions can be increased. Thereby, a decrease in temperature of these portions can be prevented, and the occurrence of nonuniformity in temperature of the exothermic part 13 can be prevented.

The thermocoagulation/cutting device 11 includes the first chamfered portion 44 which is provided on the outside of the portion at which the exothermic part 13 and first current supply portion 41 intersect, and the second chamfered portion 45 which is provided on the outside of the portion at which the exothermic part 13 and second current supply portion 42 intersect. According to this structure, it is possible to easily realize the structure which reduces the width of the portion at which the exothermic part 13 and first current supply portion 41 intersect, and the width of the portion at which the exothermic part 13 and second current supply portion 42 intersect.

The dimension of the exothermic part 13 in the direction crossing the longitudinal direction of the exothermic part 13 is less than the dimension of the first current supply portion 41 in the direction crossing the longitudinal direction of the first current supply portion 41, the dimension of the second current supply portion 42 in the direction crossing the longitudinal direction of the second current supply portion 42, and the dimension of the third current supply portion 43 in the direction crossing the longitudinal direction of the third current supply portion 43.

According to this structure, the exothermic part 13 can be formed to have a less width than the first to third current supply portions 41 to 43. Thereby, the resistance value of the exothermic part 13 can be increased, and the exothermic part 13 side can be caused to produce heat more efficiently than the first to third current supply portions 41 to 43.

In the meantime, the current values of the electric currents flowing in the above-described path a and path b may be made different. For example, the current value of the electric current flowing in the path a may be decreased, and the current value of the electric current flowing in the path b may be increased. Thereby, for example, treatment of coagulation can be performed at low temperatures on the distal end side of the coagulation/cutting unit 21. On the proximal end side of the coagulation/cutting unit 21, for example, treatment of cutting can be performed quickly at high temperatures.

[Second Embodiment]

Referring to FIG. 11, a thermocoagulation/cutting device 11 of a second embodiment is described. The thermocoagulation/cutting device 11 of the second embodiment differs from that of the first embodiment with respect to the shape of the thermal blade 15, but the other parts are common to the first embodiment. Thus, different parts from the first embodiment will mainly be described, and illustrations or descriptions of parts common to the first embodiment are omitted.

The thermal blade 15 is integrally formed of a metallic material, for example, in a substantially "E" shape. The thermal blade 15 is formed, for example, by press working by punching a substantially "E" shaped piece out of a single metal plate.

The thermal blade 15 includes an exothermic part 13 which is linearly provided along the longitudinal direction of the first jaw 32 (grasping section); a first current supply portion 41 provided on a distal end side of the first jaw 32; a second current supply portion 42 provided on a proximal end side of the first jaw 32; and a third current supply portion 43 which projects from the exothermic part 13 at a position between the first current supply portion 41 and second current supply portion 42.

Each of the first current supply portion 41 to third current supply portion 43 is formed integral with the exothermic part 13, and projects, for example, from the exothermic part 13 in a direction crossing (perpendicular to) a direction of extension of the exothermic part 13. The thermal blade 15 includes a first notch portion 71 on an inside of a corner portion formed by the exothermic part 13 and first current supply portion 41 (a portion at which the exothermic part 13 and first current supply portion 41 intersect). The thermal blade 15 includes a second notch portion 72 on an inside of a corner portion formed by the exothermic part 13 and second current supply portion 42 (a portion at which the exothermic part 13 and second current supply portion 42 intersect). Each of the first notch portion 71 and second notch portion 72 is provided in a cut shape of a substantially "V" shape.

A dimension T1 of the exothermic part 13 with respect to a direction crossing the longitudinal direction of the exothermic part 13 is less than a dimension T2 of the first current supply portion 41 in a direction crossing the longitudinal direction of the first current supply portion 41, a dimension T3 of the second current supply portion 42 in a direction crossing the longitudinal direction of the second current supply portion 42, and a dimension T4 of the third current supply portion 43 in a direction crossing the longitudinal direction of the third current supply portion 43. In addition, in this embodiment, T2=T3=T4.

A width W1 of the portion at which the exothermic part 13 and first current supply portion 41 intersect is less than a width T2 of the other portion of the first current supply portion 41. A width W2 of the portion at which the exothermic part 13 and second current supply portion 42 intersect is less than a width T3 of the other portion of the second current supply portion 42.

If a high-frequency current of the cutting mode is caused to flow to the thermal blade 15 via the first current supply line 51 to third current supply line 53, the temperature of the thermal blade 15 rises to, for example, 200° C. to 400° C., by the resistance in the inside of the thermal blade 15. If a high-frequency current of the coagulation mode is caused to flow to the thermal blade 15, the temperature of the thermal blade 15 rises to, for example, 60° C. to 150° C., by the resistance in the inside of of the thermal blade 15.

According to the second embodiment, the thermocoagulation/cutting device 11 includes the first notch portion 71 provided on the inside of the portion at which the exothermic part 13 and first current supply portion 41 intersect, and the second notch portion 72 provided on the inside of the portion at which the exothermic part 13 and second current supply portion 42 intersect.

According to this embodiment, at the portion at which the exothermic part 13 and first current supply portion 41 intersect, and at the portion at which the exothermic part 13 and second current supply portion 42 intersect, the width can be reduced and the resistance value can be increased. Thereby, a decrease in temperature of these portions can be prevented, and the occurrence of nonuniformity in temperature of the exothermic part 13 can be prevented. Moreover, according to the above-described structure, it is possible to easily realize the structure which reduces the width of the portion at which the exothermic part 13 and first current supply portion 41 intersect, and the width of the portion at which the exothermic part 13 and second current supply portion 42 intersect. In particular, in the present embodiment, it is possible to prevent a decrease in temperature at both end portions in the longitudinal direction of the exothermic part 13, and to keep high temperatures over the entirety of the exothermic part 13.

[Third Embodiment]

Referring to FIG. 12, a thermocoagulation/cutting device 11 of a third embodiment is described. The thermocoagulation/cutting device 11 of the third embodiment differs from that of the first embodiment with respect to the shape of the thermal blade 15, but the other parts are common to the first embodiment. Thus, different parts from the first embodiment will mainly be described, and illustrations or descriptions of parts common to the first embodiment are omitted.

The thermal blade 15 is integrally formed of a metallic material, for example, in a substantially "E" shape. The thermal blade 15 is formed, for example, by press working by punching a substantially "E" shaped piece out of a single metal plate.

The thermal blade 15 includes an exothermic part 13 which is linearly provided along the longitudinal direction of the first jaw 32 (grasping section); a first current supply portion 41 provided on a distal end side of the first jaw 32 in the longitudinal direction of the first jaw 32; a second current supply portion 42 provided on a proximal end side opposite to the distal end side of the first jaw 32 in the longitudinal direction of the first jaw 32; and a third current supply portion 43 which projects from the exothermic part 13 at a position between the first current supply portion 41 and second current supply portion 42 in the longitudinal direction of the first jaw 32. The exothermic part 13 includes a first portion 13A provided between the first current supply portion 41 and third current supply portion 43, and a second portion 13B provided between the second current supply portion 42 and third current supply portion 43.

Each of the first current supply portion 41 to third current supply portion 43 is formed integral with the exothermic part 13, and projects, for example, from the exothermic part 13 in a direction crossing (perpendicular to) a direction of extension of the exothermic part 13.

The thermal blade 15 includes a first chamfered portion 44 on an outside of a corner portion formed by the exothermic part 13 and first current supply portion 41 (a portion at which the exothermic part 13 and first current supply portion 41 intersect). The thermal blade 15 includes a second chamfered portion 45 on an outside of a corner portion formed by the exothermic part 13 and second current supply portion 42 (a portion at which the exothermic part 13 and second current supply portion 42 intersect).

Specifically, the exothermic part 13 includes an exothermic part body 46, and gradient portions 47 provided at both end portions in the longitudinal direction of the exothermic part body 46. The gradient portions 47 are inclined to the exothermic part body 46 and first current supply portion 41 (or second current supply portion 42).

The dimension of the first portion 13A of the exothermic part 13 becomes smaller toward the first current supply portion 41 and becomes smaller toward the third current supply portion 43 with respect to the direction crossing the longitudinal direction of the exothermic part 13. In other words, the dimension in width of the first portion 13A of the exothermic part 13 is greatest at a middle position in the longitudinal direction of the first portion 13A (the dimension with respect to the direction crossing the longitudinal direction of the exothermic part 13 is greatest).

The dimension of the second portion 13B of the exothermic part 13 becomes smaller toward the second current supply portion 42 and becomes smaller toward the third current supply portion 43 with respect to the direction crossing the longitudinal direction of the exothermic part 13. In other words, the dimension in width of the second portion 13B of the exothermic part 13 is greatest at a middle position in the longitudinal direction of the second portion 13B (the dimension with respect to the direction crossing the longitudinal direction of the exothermic part 13 is greatest).

According to the present embodiment, the dimension of the exothermic part 13 in the direction crossing the longitudinal direction of the exothermic part 13 becomes smaller toward the first current supply portion 41 and becomes smaller toward the third current supply portion 43 in a positional range between the first current supply portion 41 and third current supply portion 43, and the dimension of the exothermic part 13 in the direction crossing the longitudinal direction of the exothermic part 13 becomes smaller toward the second current supply portion 42 and becomes smaller toward the third current supply portion 43 in a positional range between the second current supply portion 42 and third current supply portion 43.

As in the present embodiment, if the structure in which the first to third current supply portions 41 to 43 are integrally projected from the exothermic part 13 is adopted, there is a concern that the heat of the exothermic part 13 is conducted to the first to third current supply portions 41 to 43 side, and the temperature of the exothermic part 13 lowers at positions near the first to third current supply portions 41 to 43. According to this structure, the resistance value of the exothermic part 13 can be increased at positions near the first to third current supply portions 41 to 43. Thereby, the heat production amount of the exothermic part 13 can be increased at positions near the first to third current supply portions 41 to 43, taking into account, in advance, that heat escapes to the first to third current supply portions 41 to 43. Thereby, the occurrence of nonuniformity in temperature on the exothermic part 13 can be prevented.

(Modification)

The thermal blade 15 of the thermocoagulation/cutting device 11 of the present embodiment can be modified and implemented as in a modification illustrated in FIG. 13. In this modification, the dimension of the exothermic part 13 becomes smaller toward the first current supply portion 41 and becomes smaller toward the second current supply portion 42 with respect to the direction crossing the longitudinal direction of the exothermic part 13. Specifically, in the present modification, the dimension in width of the exothermic part 13 is greatest at a middle position in the longitudinal direction of the exothermic part 13 (the dimension with respect to the direction crossing the longitudinal direction of the exothermic part 13 is greatest).

According to this modification, a decrease in temperature of the exothermic part 13 can be prevented, mainly at positions near the first current supply portion 41 and second current supply portion 42. Thereby, for example, when a relatively large living body tissue 69 is grasped by the entirety of the grasping section and is coagulated or cut, it becomes possible to prevent such a situation from occurring that the temperature lowers at a position near the first current supply portion 41 or at a position near the second current supply portion 42, resulting in a failure in exhibiting a sufficient performance.

[Fourth Embodiment]

Referring to FIG. 14, a thermocoagulation/cutting device 11 of a fourth embodiment is described. The thermocoagulation/cutting device 11 of the fourth embodiment differs from that of the first embodiment with respect to the shape of the thermal blade 15, but the other parts are common to the first embodiment. Thus, different parts from the first embodiment will mainly be described, and illustrations or descriptions of parts common to the first embodiment are omitted.

The thermal blade 15 is integrally formed of a metallic material, for example, in a substantially "E" shape.

The thermal blade 15 includes an exothermic part 13 which is linearly provided along the longitudinal direction of the first jaw 32 (grasping section); a first current supply portion 41 provided on a distal end side of the first jaw 32; a second current supply portion 42 provided on a proximal end side opposite to the distal end side of the first jaw 32; and a third current supply portion 43 which projects from the exothermic part 13 at a position between the first current supply portion 41 and second current supply portion 42. The exothermic part 13 includes a first portion 13A provided between the first current supply portion 41 and third current supply portion 43, and a second portion 13B provided between the second current supply portion 42 and third current supply portion 43.

Each of the first current supply portion 41 to third current supply portion 43 is formed integral with the exothermic part 13, and projects, for example, from the exothermic part 13 in a direction crossing (perpendicular to) a direction of extension of the exothermic part 13. The third current supply portion 43 is located more on the distal end side of the first jaw 32 than a middle position of the exothermic part 13 in the longitudinal direction of the first jaw 32.

A dimension T1 of the first portion 13A with respect to a direction crossing the longitudinal direction of the exothermic part 13 is less than, for example, a dimension T2 of the first current supply portion 41 in a direction crossing the longitudinal direction of the first current supply portion 41, a dimension T3 of the second current supply portion 42 in a direction crossing the longitudinal direction of the second current supply portion 42, and a dimension T4 of the third current supply portion 43 in a direction crossing the longitudinal direction of the third current supply portion 43. In short, in this embodiment, for example, T1<T2=T3=T4.

A dimension T1' of the second portion 13B with respect to the direction crossing the longitudinal direction of the exothermic part 13 is less than the dimension T1 of the first portion 13A with respect to the direction crossing the longitudinal direction of the exothermic part 13, the dimension T2 of the first current supply portion 41 in the direction crossing the longitudinal direction of the first current supply portion 41, the dimension T3 of the second current supply portion 42 in the direction crossing the longitudinal direction of the second current supply portion 42, and the dimension T4 of the third current supply portion 43 in the direction crossing the longitudinal direction of the third current supply portion 43.

The exothermic part 13 of the thermal blade 15 is exposed to the outside. The first current supply portion 41, second current supply portion 42 and third current supply portion 43 of the thermal blade 15 are inserted in through-holes which are provided in the first insulation member 35. The first current supply portion 41 is, at a distal end portion thereof, connected to the first current supply line 51. The second current supply portion 42 is, at a distal end portion thereof, connected to the second current supply line 52. The third current supply portion 43 is, at a distal end portion thereof, connected to the third current supply line 53.

If a high-frequency current is caused to flow to the thermal blade 15 via the first current supply line 51 to third current supply line 53, the temperature of the thermal blade 15 rises by the resistance in the inside of of the thermal blade 15. In the present embodiment, since the resistance value of the first portion 13A of the exothermic part 13 is low, the first portion 13A produces heat in a range of, for example, 100° C. to 150° C. Since the resistance value of the second portion 13B of the exothermic part 13 is high, the temperature of the second portion 13B rises to, for example, 250° C. to 400° C.

Thereby, coagulation of a living body tissue can be performed by the first portion 13A which produces heat at low temperatures. On the other hand, cutting of a living body tissue can be performed by the second portion 13B which produces heat at high temperatures.

According to the present embodiment, the dimension of the exothermic part 13 with respect to the direction crossing the longitudinal direction of the exothermic part 13 in the positional range between the first current supply portion 41 and third current supply portion 43 is greater than the dimension of the exothermic part 13 with respect to the direction crossing the longitudinal direction of the exothermic part 13 in the positional range between the second current supply portion 42 and third current supply portion 43.

According to this structure, the resistance value on the distal end side of the grasping section can be decreased, and the resistance value on the proximal end side of the grasping section can be increased. Thereby, the temperature of the exothermic part 13 can be lowered on the distal end side of the grasping section, and a thermal effect on a living body tissue existing near the distal end side can be suppressed to a minimum. On the other hand, on the proximal end side opposite to the distal end side of the grasping section, the temperature of the exothermic part 13 can be raised, and treatment, such as hemostasis or cutting of, for example, a blood vessel, can exactly be performed.

In the meantime, the structure of the thermal blade 15 of the present embodiment is merely an example, and such a structure may be adopted that the dimension in width of the first portion 13A with respect to the direction crossing the longitudinal direction of the exothermic part 13 is reduced and the resistance value of the first portion 13A is increased, and the dimension in width of the second portion 13B with respect to the direction crossing the longitudinal direction of the exothermic part 13 is increased and the resistance value of the second portion 13B is decreased.

[Fifth Embodiment]

Referring to FIG. 15, a thermocoagulation/cutting device 11 of a fifth embodiment is described. The thermocoagulation/cutting device 11 of the fifth embodiment differs from that of the first embodiment with respect to the number of thermal blades, but the other parts are common to the first embodiment. Thus, different parts from the first embodiment will mainly be described, and illustrations or descriptions of parts common to the first embodiment are omitted.

A coagulation/cutting unit 21 includes a first jaw 32 (grasping section) which is provided stationary relative to the sheath section 23, a second jaw 33 (second grasping section) which is provided rotatable relative to the first jaw 32 and sheath section 23, a thermal blade 15 (first thermal blade) which is formed of a metal and is provided on a surface of the first jaw 32, and a second thermal blade 73 which is formed of a metal and is provided on a surface of the second jaw 33. The first jaw 32 includes a first jaw body 34 which is made of a metal and forms the contour of the first jaw 32, and a first insulation member 35 which is positioned inside the first jaw body 34. The exothermic part 13 of the thermal blade 15 is fixed on a raised portion of the first insulation member 35.

The second jaw 33 is supported by a pin which is fixed to a distal end portion of the sheath section 23, and is attached to be rotatable about the pin. Thus, the second jaw 33 can be meshed (engaged) with the first jaw, and can be separated from the first jaw 32. The second jaw 33 includes a second jaw body 36 which is made of a metal and forms the contour of the second jaw 33, and a second insulation member 37 which is positioned inside the second jaw body 36. A second exothermic part 74 of the second thermal blade 73 is fixed on a raised portion of the second insulation member 37.

The thermal blade 15 is integrally formed of a metallic material, for example, in a substantially "E" shape.

As illustrated in FIG. 15, a dimension T1 of the exothermic part 13 with respect to a direction crossing the longitudinal direction of the exothermic part 13 is less than a dimension T2 of the first current supply portion 41 in a direction crossing the longitudinal direction of the first current supply portion 41, a dimension T3 of the second current supply portion 42 in a direction crossing the longitudinal direction of the second current supply portion 42, and a dimension T4 of the third current supply portion 43 in a direction crossing the longitudinal direction of the third current supply portion 43. In addition, in this embodiment, T1<T2=T3=T4.

A width W1 of the portion at which the exothermic part 13 and first current supply portion 41 intersect is less than a width T2 of the other portion of the first current supply portion 41. A width W2 of the portion at which the exothermic part 13 and second current supply portion 42 intersect is less than a width T3 of the other portion of the second current supply portion 42.

The second thermal blade 73 is integrally formed of a metallic material, for example, in a substantially WE shape. The second thermal blade 73 is formed, for example, by press working by punching a substantially "E" shaped piece out of a single metal plate. The second thermal blade 73 has substantially the same structure as the thermal blade 15 of the first embodiment.

The second thermal blade 73 includes a second exothermic part 74 which is linearly provided along the longitudinal direction of the second jaw 33 (grasping section); a fourth current supply portion 75 provided on a distal end side of the second jaw 33; a fifth current supply portion 76 which is provided on a proximal end side opposite to the distal end side of the second jaw 33; and a sixth current supply portion 77 which projects from the second exothermic part 74 at a position between the fourth current supply portion 75 and fifth current supply portion 76. The second exothermic part 74 includes a third portion 74A provided between the fourth current supply portion 75 and sixth current supply portion 77, and a fourth portion 74B provided between the fifth current supply portion 76 and sixth current supply portion 77.

Each of the fourth current supply portion 75 to sixth current supply portion 77 is formed integral with the second exothermic part 74, and projects, for example, from the second exothermic part 74 in a direction crossing (perpendicular to) a direction of extension of the second exothermic part 74. In other words, each of the fourth current supply portion 75 to sixth current supply portion 77 projects integrally from the second exothermic part 74. The sixth current supply portion 77 is located more on the distal end side of the second jaw 33 than a middle position of the second exothermic part 74 in the longitudinal direction of the second jaw 33.

The second thermal blade 73 includes a third chamfered portion 78 on an outside of a corner portion formed by the second exothermic part 74 and fourth current supply portion 75 (a portion at which the second exothermic part 74 and fourth current supply portion 75 intersect). The second thermal blade 73 includes a fourth chamfered portion 79 on an outside of a corner portion formed by the second exothermic part 74 and fifth current supply portion 76 (a portion at which the second exothermic part 74 and fifth current supply portion 76 intersect).

Specifically, the second exothermic part 74 includes a second exothermic part body 46, and second gradient portions 81 provided at both end portions in the longitudinal direction of the second exothermic part body 46. The second gradient portions 81 are inclined to the second exothermic part body 46 and fourth current supply portion 75 (or fifth current supply portion 76).

A dimension T5 of the second exothermic part 74 with respect to a direction crossing the longitudinal direction of the second exothermic part 74 is less than, for example, a dimension T6 of the fourth current supply portion 75 in a direction crossing the longitudinal direction of the fourth current supply portion 75, a dimension T7 of the fifth current supply portion 76 in a direction crossing the longitudinal direction of the fifth current supply portion 76, and a dimension T8 of the sixth current supply portion 77 in a direction crossing the longitudinal direction of the sixth current supply portion 77. The dimension T5 is less than, for example, the dimension T1 of the exothermic part 13 with respect to the direction crossing the longitudinal direction of the exothermic part 13.

A width W3 of the portion at which the second exothermic part 74 and fourth current supply portion 75 intersect is less than a width T6 of the other portion of the fourth current supply portion 75. A width W4 of the portion at which the second exothermic part 74 and fifth current supply portion 76 intersect is less than a width T7 of the other portion of the fifth current supply portion 76.

The second exothermic part 74 of the second thermal blade 73 is exposed to the outside. The fourth current supply portion 75, fifth current supply portion 76 and sixth current supply portion 77 of the second thermal blade 73 are inserted in through-holes which are provided in the second insulation member 37. The fourth current supply portion 75 is, at a distal end portion thereof, connected to a fourth current supply line 82. The fifth current supply portion 76 is, at a distal end portion thereof, connected to a fifth current supply line 84. The sixth current supply portion 77 is, at a distal end portion thereof, connected to a sixth current supply line 83.

The fourth current supply line 82 to the sixth current supply line 84 extend through a gap between the second jaw body 36 and second insulation member 37, and are connected to the output connector 54 of the controller 16 of the power supply device 14 through the inside of the sheath section 23 (insulation tube 31A) and the inside of the cylindrical portion 26 of the handle unit 22.

The relay switching circuit 63 of the controller 16 can select two current supply lines from the fourth current supply line 82 to sixth current supply line 84, and can cause a high-frequency current to flow through them. Similarly, the relay switching circuit 63 can select two current supply lines from the first to third current supply lines 51 to 53, and can cause a high-frequency current to flow through them. Furthermore, the relay switching circuit 63 can select two current supply lines from the first to third current supply lines 51 to 53, and can cause a high-frequency current to flow through them, and, at the same time, can select two current supply lines from the fourth current supply line 82 to sixth current supply line 84, and can cause a high-frequency current to flow through them.

Specifically, in the present embodiment, although both the thermal blade 15 and second thermal blade 73 can be caused to produce heat, it is also possible to cause either the thermal blade 15 or second thermal blade 73 to produce heat independently. In this embodiment, in accordance with the purpose of use, a part of the thermal blade 15 and a part of the second thermal blade 73 can be caused to produce heat in combination, and the temperature may be varied from part to part of the coagulation/cutting unit 21.

For example, when the entirety of the coagulation/cutting unit 21 is to be caused to produce heat at low temperatures, a current is caused to flow between the first current supply portion 41 and second current supply portion 42 of the thermal blade 15 which has a low resistance value, and the entirety of the exothermic part 13 is caused to produce heat at relatively low temperatures (e.g. 100° C. to 150° C.). Thereby, coagulation of a living body tissue can be performed by the entirety of the exothermic part 13. When the entirety of the coagulation/cutting unit 21 is to be caused to produce heat at high temperatures, a current is caused to flow between the fourth current supply portion 75 and fifth current supply portion 76 of the second thermal blade 73 which has a high resistance value, and the entirety of the second exothermic part 74 is caused to produce heat at relatively high temperatures (e.g. 250° C. to 400° C.). Thereby, cutting of a living body tissue can be performed by the entirety of the second exothermic part 74.

When the distal end side of the coagulation/cutting unit 21 is to be caused to produce heat at low temperatures and the proximal end side opposite to the distal end side is to be caused to produce heat at high temperatures, a current is caused to flow between the first current supply portion 41 and third current supply portion 43 of the thermal blade 15 which has a low resistance value, and the first portion 13A of the exothermic part 13 is caused to produce heat at relatively low temperatures (e.g. 100° C. to 150° C.). Thereby, coagulation of a living body tissue can be performed by the first portion 13A. In addition, a current is caused to flow between the fifth current supply portion 76 and sixth current supply portion 77 of the thermal blade 15 which has a high resistance value, and the fourth portion 74B of the second exothermic part 74 is caused to produce heat at relatively high temperatures (e.g. 250° C. to 400° C.). Thereby, cutting of a living body tissue can be performed by the fourth portion 74B. Therefore, the same advantageous effects as in the fourth embodiment can be obtained.

On the other hand, the distal end side of the coagulation/cutting unit 21 can be caused to produce heat at high temperatures, and the proximal end side can be caused to produce heat at low temperatures. In this case, a current is caused to flow between the fourth current supply portion 75 and sixth current supply portion 77 of the second thermal blade 73 which has a high resistance value, and the third portion 74A of the second exothermic part 74 is caused to produce heat at relatively high temperatures (e.g. 250° C. to 400° C.). Thereby, cutting of a living body tissue can be performed by the third portion 74A. In addition, a current is caused to flow between the second current supply portion 42 and third current supply portion 43 of the thermal blade 15 which has a low resistance value, and the second portion 13B of the exothermic part 13 is caused to produce heat at relatively low temperatures (e.g. 100° C. to 150° C.). Thereby, coagulation of a living body tissue can be performed by the second portion 13B.

According to the fifth embodiment, the thermocoagulation/cutting device 11 includes the rod-shaped second grasping section which is opposed to the above-described grasping section; the second exothermic part 74 which is formed of a metal, is provided on the surface of the second grasping section linearly along the longitudinal direction of the second grasping section, and is opposed to the exothermic part 13; the fourth current supply portion 75 projecting integrally from the second exothermic part 74 on the distal end side of the second grasping section in the longitudinal direction of the second grasping section; the fifth current supply portion 76 projecting integrally from the second exothermic part 74 on the proximal end side of the grasping section in the longitudinal direction of the second grasping section; the sixth current supply portion 77 projecting integrally from the second exothermic part 74 at a position between the fourth current supply portion 75 and fifth current supply portion 76 in the longitudinal direction of the second grasping section; and the controller 16 which is connected to the fourth current supply portion 75, fifth current supply portion 76 and sixth current supply portion 77 and causes an electric current to flow between the fourth current supply portion 75 and fifth current supply portion 76, between the fourth current supply portion 75 and sixth current supply portion 77, or between the fifth current supply portion 76 and sixth current supply portion 77.

According to this structure, since the exothermic part 13 and the second exothermic part 74, which is opposed to the exothermic part 13, are provided, heat can be applied from two directions to the living body tissue which is grasped between the grasping section and the second grasping section (between the exothermic part 13 and the second exothermic part 74). Thereby, the time that is needed for coagulation or cutting of the living body tissue can be shortened. Hence, the thermal effect on a living body tissue existing near the treatment part can be decreased. Moreover, since the second grasping section can be meshed (engaged) with, and can be separated from, the first grasping section, a tissue can be ripped or held in accordance with purposes.

The dimension of the first portion 13A of the exothermic part 13, which is located between the first current supply portion 41 and third current supply portion 43, with respect to the direction crossing the longitudinal direction of the exothermic part 13, is different from the dimension of the third portion 74A of the second exothermic part 74, which is located between the fourth current supply portion 75 and sixth current supply portion 77 and is opposed to the first portion 13A, with respect to the direction crossing the longitudinal direction of the second exothermic part 74. The dimension of the second portion 13B of the exothermic part 13, which is located between the second current supply portion 42 and third current supply portion 43, with respect to the direction crossing the longitudinal direction of the exothermic part 13, is different from the dimension of the fourth portion 74B of the second exothermic part 74, which is located between the fifth current supply portion 76 and sixth current supply portion 77 and is opposed to the second portion 13B, with respect to the direction crossing the longitudinal direction of the second exothermic part 74.

According to this structure, the resistance value of a portion of the exothermic part 13 is made different from the resistance value of that portion of the second exothermic part 74, which is opposed to the portion of the exothermic part 13. Hence, by properly switching the exothermic part 13 (74) that is used, a living body tissue can be coagulated or cut at proper temperatures in accordance with purposes of use. Specifically, when treatment of coagulation or cutting is to be carefully performed at low temperatures by the distal end side or proximal end side in the longitudinal direction of the grasping section, or by the entirety of the grasping section, the exothermic part 13 with a lower resistance value can be selected and used. On the other hand, when treatment of coagulation or cutting is to be quickly performed at high temperatures by the distal end side or proximal end side in the longitudinal direction of the grasping section, or by the entirety of the grasping section, the exothermic part (second exothermic part 74) with a higher resistance value can be selected and used.

(Modification)

The thermal blade 15 of the thermocoagulation/cutting device 11 of the present embodiment can be modified and implemented as in a modification illustrated in FIG. 16. In this modification, the width of the second portion 13B of the exothermic part 13 and the width of the fourth portion 74B of the second exothermic part 74 are different from those in the fifth embodiment. Thus, in the description below, different parts from the fifth embodiment will mainly be described, and descriptions of parts common to the fifth embodiment are omitted.

A dimension T1 of the first portion 13A of the exothermic part 13 with respect to the direction crossing the longitudinal direction of the exothermic part 13 is less than, for example, the dimension T2 of the first current supply portion 41 in the direction crossing the longitudinal direction of the first current supply portion 41, the dimension T3 of the second current supply portion 42 in the direction crossing the longitudinal direction of the second current supply portion 42, and the dimension T4 of the third current supply portion 43 in the direction crossing the longitudinal direction of the third current supply portion 43. In short, T1<T2=T3=T4. In addition, a dimension T1' of the second portion 13B of the exothermic part 13 with respect to the direction crossing the longitudinal direction of the exothermic part 13 is less than, for example, the dimension T2, dimension T3 and dimension T4.

A dimension T5 of the third portion 74A of the second exothermic part 74 with respect to the direction crossing the longitudinal direction of the second exothermic part 74 is less than, for example, the dimension T6 of the fourth current supply portion 75 in the direction crossing the longitudinal direction of the fourth current supply portion 75, the dimension T7 of the fifth current supply portion 76 in the direction crossing the longitudinal direction of the fifth current supply portion 76, and the dimension T8 of the sixth current supply portion 77 in the direction crossing the longitudinal direction of the sixth current supply portion 77. In addition, the dimension T5 is less than the dimension T1 of the first portion 13A of the exothermic part 13.

A dimension T5' of the fourth portion 74B of the second exothermic part 74 with respect to the direction crossing the longitudinal direction of the second exothermic part 74 is less than, for example, the dimension T6, dimension T7 and dimension T8. In short, T5'<T6=T7=T8. In addition, the dimension T5' is greater than the dimension T1' of the second portion 13B of the exothermic part 13.

According to the present modification, too, the resistance value of a portion of the exothermic part 13 is made different from the resistance value of that portion of the second exothermic part 74, which is opposed to the portion of the exothermic part 13. Hence, by properly switching the exothermic part 13 that is used, a living body tissue can be coagulated or cut at proper temperatures in accordance with purposes of use. Specifically, when treatment of coagulation or cutting is to be carefully performed at low temperatures by the distal end side or proximal end side in the longitudinal direction of the grasping section, or by the entirety of the grasping section, the exothermic part with a lower resistance value can be selected and used. On the other hand, when treatment of coagulation or cutting is to be quickly performed at high temperatures by the distal end side or proximal end side in the longitudinal direction of the grasping section, or by the entirety of the grasping section, the exothermic part with a higher resistance value can be selected and used.

[Sixth Embodiment]

Figure 17:
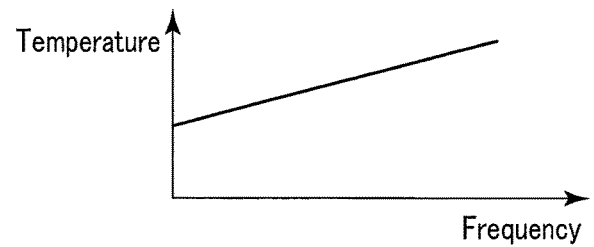
FIG. 17 is a graph showing a relationship (frequency characteristic) between a current frequency and a temperature of a thermal blade of a thermocoagulation/cutting device of a sixth embodiment.
Figure 18:
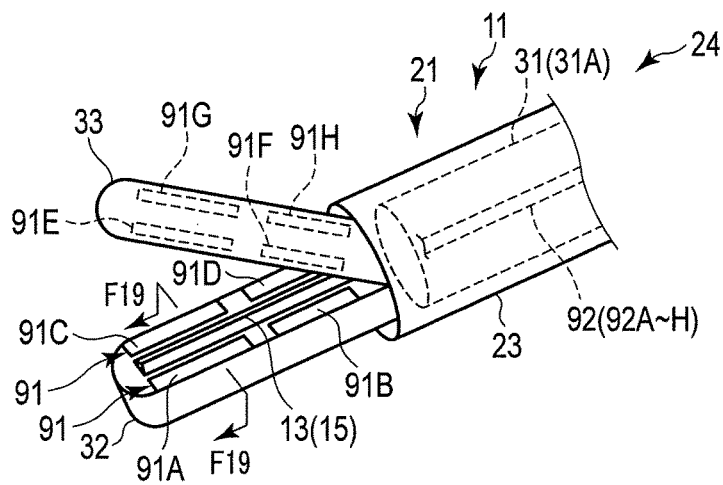
FIG. 18 is a perspective view illustrating a coagulation/cutting unit of a thermocoagulation/cutting device of a seventh embodiment.
Figure 19:
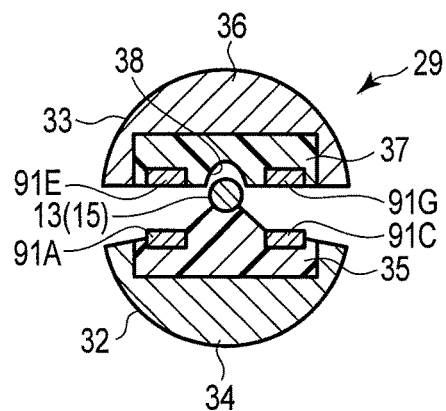
FIG. 19 is a cross-sectional view of the coagulation/cutting unit shown in FIG. 18, FIG. 19 being taken along line F19-F19 in FIG. 18.

Referring to FIG. 17, a thermocoagulation/cutting device 11 of a sixth embodiment is described. The thermocoagulation/cutting device 11 of the sixth embodiment differs from that of the first embodiment in that the frequency characteristic of the thermal blade 15 is different, but the other parts are common to the first embodiment. Thus, different parts from the first embodiment will mainly be described, and illustrations or descriptions of parts common to the first embodiment are omitted.

In the present embodiment, the thermal blade 15 is formed by adopting a metallic material with a frequency characteristic. As the metallic material with the frequency characteristic, a Fe—Cr—Al alloy, for instance, is usable, but other metallic materials with frequency characteristics are also usable. As illustrated in FIG. 17, this metallic material has such a characteristic that, even if the current value of a flowing electric current is the same, the resistance (as a result, the temperature of the exothermic part 13) varies (rises) in accordance with an increase in frequency.

In the present embodiment, the controller 16 causes an electric current having, for example, a predetermined current value and a relatively low frequency (less than 400 KHz) to flow between, for example, the first current supply portion 41 and third current supply portion 43, thereby causing the first portion 13A of the exothermic part 13 to produce heat at relatively low temperatures (e.g. 100° C. to 150° C.). Thereby, a living body tissue can be coagulated by the first portion 13A. In addition, the controller 16 causes an electric current having, for example, a predetermined current value and a relatively high frequency (400 KHz or more) to flow between the second current supply portion 42 and third current supply portion 43, thereby causing the second portion 13B of the exothermic part 13 to produce heat at relatively high temperatures (e.g. 250° C. to 400° C.). Thereby, a living body tissue can be cut by the second portion 13B.

In the meantime, the above is merely an example, and the relationship between the temperature of the first portion 13A and the temperature of the second portion 13B may be reversed, and a modification may be implemented. Specifically, in this modification, the controller 16 causes an electric current having, for example, a predetermined current value and a relatively high frequency (400 KHz or more) to flow between the first current supply portion 41 and third current supply portion 43, thereby causing the first portion of the exothermic part 13 to produce heat at relatively high temperatures (e.g. 250° C. to 400° C.). In addition, the controller 16 causes an electric current having, for example, a predetermined current value and a relatively low frequency (less than 400 KHz) to flow between the second current supply portion 42 and third current supply portion 43, thereby causing the second portion 13B of the exothermic part 13 to produce heat at relatively low temperatures (e.g. 100° C. to 150° C.). Thereby, a living body tissue can be coagulated by the second portion 13B.

According to the present embodiment, the thermocoagulation/cutting device 11 includes the rod-shaped grasping section; the exothermic part 13 which is provided on the surface of the grasping section linearly along the longitudinal direction of the grasping section and is formed of a metal having such a characteristic that a resistance varies in accordance with a variation in frequency of an electric current; the first current supply portion 41 projecting integrally from the exothermic part 13 on the distal end side of the grasping section; the second current supply portion 42 projecting integrally from the exothermic part 13 on the proximal end side of the grasping section; the third current supply portion 43 projecting integrally from the exothermic part 13 at a position between the first current supply portion 41 and second current supply portion 42; and the controller 16 which is connected to the first current supply portion 41, second current supply portion 42 and third current supply portion 43 and causes electric currents with mutually different frequencies to flow between the first current supply portion 41 and third current supply portion 43 and between the second current supply portion 42 and third current supply portion 43.

According to this structure, the output frequency of an electric current flowing between the first current supply portion 41 and third current supply portion 43 of the exothermic part 13 is made different from the output frequency of an electric current flowing between the second current supply portion 42 and third current supply portion 43. Thereby, the temperature between the first current supply portion 41 and third current supply portion 43 can easily be made different from the temperature between the second current supply portion 42 and third current supply portion 43. Specifically, in the present embodiment, by varying the amplitude (current value) of the output current and the frequency of the output current, the temperature between the first current supply portion 41 and third current supply portion 43 of the exothermic part 13 and the temperature between the second current supply portion 42 and third current supply portion 43 can be controlled more finely.

[Seventh Embodiment]

Referring to FIG. 18 to FIG. 21, a thermocoagulation/cutting device 11 of a seventh embodiment is described. The thermocoagulation/cutting device 11 of the seventh embodiment differs from that of the first embodiment in that the coagulation/cutting unit 21 is provided with a plurality of HF electrodes 91, and that the power supply device 14 includes a second controller 90 for HF electrodes. However, the other parts are common to the first embodiment. Thus, different parts from the first embodiment will mainly be described, and illustrations or descriptions of parts common to the first embodiment are omitted.

The coagulation/cutting unit 21 includes a first jaw 32 (grasping section) which is provided stationary relative to the sheath section 23, a second jaw 33 (second grasping section) which is provided rotatable relative to the first jaw 32 and sheath section 23, a thermal blade 15 which is formed of a metal and is provided on a surface of the first jaw 32, and a plurality of HF electrodes 91 (high-frequency electrodes) provided on surfaces of the first jaw 32 and second jaw 33. The first jaw 32 is provided, for example, in a rod shape with a semicircular cross section. The first jaw 32 includes a first jaw body 34 which is made of a metal and forms the contour of the first jaw 32, and a first insulation member 35 which is positioned inside the first jaw body 34. The exothermic part 13 of the thermal blade 15 is fixed on a raised portion of the first insulation member 35. The HF electrodes 91 are provided on both sides of the thermal blade 15 on the surface of the first insulation member 35. In the present embodiment, the HF electrodes 91 are arranged in two rows along the longitudinal direction of the first jaw 32. Each of these rows includes a plurality of HF electrodes 91. In this embodiment, for example, two HF electrodes 91 are provided in each row, but the number of HF electrodes 91 may be three or more. In the present embodiment, a first HF electrode 91A, a second HF electrode 91B, a third HF electrode 91C and a fourth HF electrode 91D are disposed on the first jaw 32 side. The first HF electrode 91A and third HF electrode 91C correspond to the first portion 13A of the exothermic part 13. The second HF electrode 91B and fourth HF electrode 91D correspond to the second portion 13B of the exothermic part 13.

The second jaw 33 is provided, for example, in a rod shape with a semicircular cross section. The second jaw 33 is supported by a pin which is fixed to a distal end portion of the sheath section 23. The second jaw 33 includes a second jaw body 36 which is made of a metal and forms the contour of the second jaw 33, a second insulation member 37 which is positioned inside the second jaw body 36, and a groove portion 38 which is provided in the second insulation member 37 and in which the thermal blade 15 is fitted when the first jaw 32 and second jaw 33 are engaged. The groove portion 38 extends in the longitudinal direction of the second jaw 33 so as to correspond to the thermal blade 15.

The HF electrodes 91 are provided on both sides of the groove portion 38 on the surface of the second insulation member 37. In the present embodiment, the HF electrodes 91 are arranged in two rows along the longitudinal direction of the second jaw 33. Each of these rows includes a plurality of HF electrodes 91. In this embodiment, for example, two HF electrodes 91 are provided in each row, but the number of HF electrodes 91 may be three or more. In the present embodiment, a fifth HF electrode 91E, a sixth HF electrode 91F, a seventh HF electrode 91G and an eighth HF electrode 91H are disposed on the second jaw 33 side.

The fifth HF electrode 91E is opposed to the first HF electrode 91A on the first jaw 32 side. The sixth HF electrode 91F is opposed to the second HF electrode 91B on the first jaw 32 side. The seventh HF electrode 91G is opposed to the third HF electrode 91C on the first jaw 32 side. The eighth HF electrode 91H is opposed to the fourth HF electrode 91D on the first jaw 32 side. The first HF electrode 91A to eighth HF electrode 91H are examples of a plurality of detectors which can detect the position of a living body tissue.

The thermal blade 15 is integrally formed of a metallic material, for example, in a substantially "E" shape. The details of the structure of the thermal blade 15 are the same as in the first embodiment.

The thermocoagulation/cutting device 11 includes a plurality of HF supply lines 92 which connect the HF electrodes 91 and output connector 54. To be more specific, the thermocoagulation/cutting device 11 includes a first HF supply line 92A which connects the first HF electrode 91A and output connector 54, a second HF supply line 92B which connects the second HF electrode 91B and output connector 54, a third HF supply line 92C which connects the third HF electrode 91C and output connector 54, and a fourth HF supply line 92D which connects the fourth HF electrode 91D and output connector 54.

The first HF supply line 92A to fourth HF supply line 92D extend through a gap between the first jaw body 34 and first insulation member 35, and are connected to the output connector 54 of the second controller 90 through the inside of the sheath section 23 (insulation tube 31A) and the inside of the cylindrical portion 26 of the handle unit 22.

The thermocoagulation/cutting device 11 includes a fifth HF supply line 92E which connects the fifth HF electrode 91E and output connector 54, a sixth HF supply line 92F which connects the sixth HF electrode 91F and output connector 54, a seventh HF supply line 92G which connects the seventh HF electrode 91G and output connector 54, and an eighth HF supply line 92H which connects the eighth HF electrode 91H and output connector 54.

The fifth HF supply line 92E to eighth HF supply line 92H extend through a gap between the second jaw body 36 and second insulation member 37, and are connected to the output connector 54 of the power supply device 14 through the inside of the sheath section 23 (insulation tube 31A) and the inside of the cylindrical portion of the handle unit 22.

Next, referring to FIG. 21, a description is given of the structure of the second controller 90 of the power supply device 14 of the thermocoagulation/cutting device 11 of the embodiment. The second controller 90 includes partial structures which are also utilized in the above-described controller 16, and is realized within the power supply device 14. The second controller 90 has substantially the same structure as the controller 16.

The second controller 90 of the power supply device 14 includes a CPU 55, a power supply circuit 56, a resonance circuit 57, a waveform generation circuit 58, an amplifier 61, an output transformer 62, a relay switching circuit 63, the output connector 54, a current detection circuit 64, a voltage detection circuit 65, a communication circuit 66, and a communication connector 67.

The waveform generation circuit 58 generates a sine wave and a burst wave. A signal of the sine wave or burst wave, which is output from the waveform generation circuit 58, is input to the amplifier circuit 61 via the resonance circuit 57. The signal amplified by the amplifier 61 is applied to a primary winding side of the output transformer 62, and a high-frequency signal, which is a high-frequency output for the HF electrodes 91, occurs on a secondary winding side of the output transformer 62.

The secondary winding of the output transformer 62 is connected to the output connector 54 which is integrated into, for example, a single unit, via the relay switching circuit 63 which switches a high-frequency signal that is output. The first HF supply line 92A to eighth HF supply line 92H are connected to the output connector 54. The relay switching circuit 63 can select a pair of HF supply lines 92 (from first HF supply line 92A to eighth HF supply line 92H) which correspond to two HF electrodes 91 that are opposed, as described above, between the first jaw 32 and second jaw 33, and can cause a high-frequency current to flow through them.

In addition, the resonance circuit 57 is supplied with a power supply voltage from the power supply circuit 56 which is capable of varying a voltage, and the waveform generation circuit 58 and power supply circuit 56 are controlled by a central processing unit (hereinafter referred to as CPU 55) that is the controller 16. The CPU 55 controls the waveform generation circuit 58 and power supply circuit 56 in accordance with the setting of an output mode, an output set value, etc. The output signal of the secondary winding of the output transformer 62 is input to the voltage detection circuit 65 and current detection circuit 64, which constitute a detection unit.

The voltage detection circuit 65 and current detection circuit 64 detect, that is, measure, the voltage and current of the high-frequency signal which is output from the secondary winding of the output transformer 62. The detected voltage and current are converted to a digital voltage signal and a digital current signal by analog-to-digital converters (hereinafter referred to as A/D converters), respectively, and the digital voltage signal and current signal are input to the CPU.

Based on the input voltage signal and current signal, the CPU 55 determines whether a living body tissue exists between two opposed HF electrodes 91. Specifically, when a high-frequency current flows between the two opposed HF electrodes 91, the CPU 55 determines (detects) that a living body tissue exits therebetween.

Furthermore, the CPU 55 is connected to the communication connector 67 via the communication circuit 66 which executes communication. This communication connector 67 is connected via a communication cable to a communication connector which exists on the handle unit 22 side.

Referring to FIG. 20, a concrete heat production control of the thermal blade 15 is described. If the thermocoagulation/cutting device 11 is activated and transitions to a treatment standby state, the second controller 90 applies, at regular time intervals, a high-frequency voltage between the first HF electrode 91A and fifth HF electrode 91E, between the second HF electrode 91B and sixth HF electrode 91F, between the third HF electrode 91C and seventh HF electrode 91G, and between the fourth HF electrode 91D and eighth HF electrode 91H. At this time, for example, if a high-frequency current flows between the first HF electrode 91A and fifth HF electrode 91E, or between the third HF electrode 91C and seventh HF electrode 91G, the second controller 90 determines (detects) that a living body tissue exists on the distal end side of the first jaw 32 and second jaw 33, which is in the vicinity of them.

At this time, based on this detection result, the controller 16 causes an electric current to flow between the first current supply portion 41 and third current supply portion 43, and causes the first portion 13A of the exothermic part 13 to produce heat. Thereby, the exothermic part 13 can be caused to produce heat on the distal end side of the first jaw 32 and second jaw 33 which clamp the living body tissue, and treatment of cutting or coagulation can be performed on the living body tissue.

Similarly, for example, if a high-frequency current flows between the second HF electrode 91B and sixth HF electrode 91F, or between the fourth HF electrode 91D and eighth HF electrode 91H, the second controller 90 determines (detects) that a living body tissue exists on the proximal end side of the first jaw 32 and second jaw 33, which is in the vicinity of them. At this time, based on this detection result, the controller 16 causes an electric current to flow between the second current supply portion 42 and third current supply portion 43, and causes the second portion 13B of the exothermic part 13 to produce heat. Thereby, the exothermic part 13 can be caused to produce heat on the proximal end side of the first jaw 32 and second jaw 33 which clamp the living body tissue, and treatment of cutting or coagulation can be performed on the living body tissue.

Furthermore, if a high-frequency current flows at least either between the first HF electrode 91A and fifth HF electrode 91E, or between the third HF electrode 91C and seventh HF electrode 91G, and if a high-frequency current flows at least either between the second HF electrode 91B and sixth HF electrode 91F, or between the fourth HF electrode 91D and eighth HF electrode 91H, the second controller 90 determines (detects) that a living body tissue is clamped by the entirety of the first jaw 32 and second jaw 33. At this time, based on this detection result, the controller 16 causes an electric current to flow between the first current supply portion 41 and second current supply portion 42, and causes the entirety of the exothermic part 13 to produce heat. Thereby, the exothermic part 13 can be caused to produce heat over the entirety of the first jaw 32 and second jaw 33 which clamp the living body tissue, and treatment of cutting or coagulation can be performed on the living body tissue.

According to the present embodiment, the thermocoagulation/cutting device 11 includes the rod-shaped grasping section; the exothermic part 13 which is formed of a metal and is provided on the surface of the grasping section linearly along the longitudinal direction of the grasping section; the first current supply portion 41 projecting integrally from the exothermic part 13 on the distal end side of the grasping section in the longitudinal direction of the grasping section; the second current supply portion 42 projecting integrally from the exothermic part 13 on the proximal end side of the grasping section in the longitudinal direction of the grasping section; the third current supply portion 43 projecting integrally from the exothermic part 13 at a position between the first current supply portion 41 and second current supply portion 42 in the longitudinal direction of the grasping section; the plural detectors which are provided on the surface of the grasping section along the longitudinal direction of the grasping section and are capable of detecting the position of the living body tissue; and the controller which is connected to the first current supply portion 41, second current supply portion 42 and third current supply portion 43 and causes, based on the detection result of the detectors, an electric current to flow between the first current supply portion 41 and second current supply portion 42, between the first current supply portion 41 and third current supply portion 43, or between the second current supply portion 42 and third current supply portion 43.

According to this structure, the exothermic part 13 can be caused to properly produce heat at a position where the living body tissue exits. Thereby, a location where the exothermic part 13 produces heat can be minimized, and the thermal effect on a living body tissue existing near the treatment part can be minimized.

In the meantime, in the present embodiment, the second controller 90 has been described as being distinguished from the controller 16. However, the controller 16 and second controller 90 may be realized by a single controller.

The present invention is not limited to the above-described embodiments, and modifications may be implemented where necessary, without departing from the spirit of the invention. In the seventh embodiment, the plural HF electrodes 91 are used for detecting a living body tissue. However, by causing a high-frequency current to flow to the living body tissue by using these HF electrodes, the temperature of the living body tissue that is a treatment target can be raised in a short time. According to this method, the coagulation or cutting by the thermal blade 15 can be assisted by the high-frequency current flowing from the HF electrodes 91. Thereby, the time during which heat is applied to a tissue near the treatment part can be shortened, and the thermal effect on the tissue near the treatment part can be decreased. Moreover, needless to say, the thermocoagulation/cutting devices 11 of the above-described embodiments can be combined to constitute a single thermocoagulation/cutting device 11.

Hereinafter, an additional description will be given of other thermocoagulation/cutting devices which realize the present invention.

[1]

A thermocoagulation/cutting device including:
a grasping section;
an exothermic part provided on the grasping section;
a first current supply portion projecting from the exothermic part on a distal end side;
a second current supply portion projecting from the exothermic part on a proximal end side;
a third current supply portion projecting from the exothermic part at a position between the first current supply portion and the second current supply portion; and
a controller configured to be capable of causing an electric current to flow between the first current supply portion and the second current supply portion, between the first current supply portion and the third current supply portion, or between the second current supply portion and the third current supply portion.

[2]

A thermocoagulation/cutting device including:
a grasping section;
an exothermic part provided on the grasping section and configured such that a temperature varies in accordance with a variation in frequency of an electric current;
a first current supply portion projecting integrally from the exothermic part on a distal end side;
a second current supply portion projecting integrally from the exothermic part on a proximal end side;
a third current supply portion projecting integrally from the exothermic part at a position between the first current supply portion and the second current supply portion in a longitudinal direction of the grasping section; and
a controller configured to cause electric currents with mutually different frequencies to flow between the first current supply portion and the third current supply portion and between the second current supply portion and the third current supply portion.

[3]

A thermocoagulation/cutting device including:
a grasping section;
an exothermic part provided on the grasping section;
a first current supply portion projecting from the exothermic part on a distal end side;
a second current supply portion projecting from the exothermic part on a proximal end side;
a third current supply portion projecting from the exothermic part at a position between the first current supply portion and the second current supply portion;
a detector provided on the grasping section; and
a controller configured to cause, based on a detection result of the detector, an electric current to flow between the first current supply portion and the second current supply portion, between the first current supply portion and the third current supply portion, or between the second current supply portion and the third current supply portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

11 . . . Thermocoagulation/cutting device, 13 . . . Exothermic part, 13A . . . First portion, 13B . . . Second portion, 16 . . . Controller, 21 . . . Coagulation/cutting unit, 32 . . . First jaw, 33 . . . Second jaw, 41 . . . First current supply portion, 42 . . . Second current supply portion, 43 . . . Third current supply portion, 44 . . . First chamfered portion, 45 . . . Second chamfered portion, 71 . . . First notch portion, 72 . . . Second notch portion, 74 . . . Second exothermic part, 74A . . . Third portion, 74B . . . Fourth portion, 75 . . . Fourth current supply portion, 76 . . . Fifth current supply portion, 77 . . . Sixth current supply portion, 91 . . . HF electrode, 91A . . . First HF electrode, 91B . . . Second HF electrode, 91C . . . Third HF electrode, 91D . . . Fourth HF electrode, 91E . . . Fifth HF electrode, 91F . . . Sixth HF electrode, 91G . . . Seventh HF electrode, 91H . . . Eighth HF electrode.

What is claimed is:

1. A thermocoagulation/cutting device comprising:
a first jaw;
an exothermic part provided on a surface of the first jaw along a longitudinal direction of the first jaw;
a first current supply portion projecting integrally from the exothermic part on a distal end side of the first jaw;
a second current supply portion projecting integrally from the exothermic part on a proximal end side of the first jaw;
a third current supply portion projecting integrally from the exothermic part at a position between the first current supply portion and the second current supply portion; and
a controller electrically connected to the first current supply portion, the second current supply portion and the third current supply portion, the controller being configured to cause an electric current to flow, in the exothermic part, between: (A) the first current supply portion and the second current supply portion, (B) the first current supply portion and the third current supply portion, or (C) the second current supply portion and the third current supply portion, wherein:
a dimension of the exothermic part in a direction crossing a longitudinal direction of the exothermic part is less than: (i) a dimension of the first current supply portion in a direction crossing a longitudinal direction of the first current supply portion, (ii) a dimension of the second current supply portion in a direction crossing a longitudinal direction of the second current supply portion, and (iii) a dimension of the third current supply portion in a direction crossing a longitudinal direction of the third current supply portion.

2. The thermocoagulation/cutting device of claim 1, wherein:
a width of a portion at which the exothermic part and the first current supply portion intersect is less than a width of the other portion of the first current supply portion, and
a width of a portion at which the exothermic part and the second current supply portion intersect is less than a width of the other portion of the second current supply portion.

3. The thermocoagulation/cutting device of claim 1, comprising:
a first chamfered portion provided on an outside of a portion at which the exothermic part and the first current supply portion intersect; and
a second chamfered portion provided on an outside of a portion at which the exothermic part and the second current supply portion intersect.

4. The thermocoagulation/cutting device of claim 1, comprising:
a first notch portion provided on an inside of a portion at which the exothermic part and the first current supply portion intersect; and
a second notch portion provided on an inside of a portion at which the exothermic part and the second current supply portion intersect.

5. The thermocoagulation/cutting device of claim 1, wherein:
the dimension of the exothermic part in the direction crossing the longitudinal direction of the exothermic part becomes smaller toward the first current supply portion and becomes smaller toward the third current supply portion in a positional range between the first current supply portion and the third current supply portion, and
the dimension of the exothermic part in the direction crossing the longitudinal direction of the exothermic part becomes smaller toward the second current supply portion and becomes smaller toward the third current supply portion in a positional range between the second current supply portion and the third current supply portion.

6. The thermocoagulation/cutting device of claim 1, wherein the dimension of the exothermic part with respect to the direction crossing the longitudinal direction of the exothermic part in the positional range between the first current supply portion and the third current supply portion is greater than the dimension of the exothermic part with respect to the direction crossing the longitudinal direction of the exothermic part in the positional range between the second current supply portion and the third current supply portion.

7. The thermocoagulation/cutting device of claim 1, comprising:
a second jaw opposed to the first jaw;
a second exothermic part opposed to the exothermic part and provided on a surface of the second jaw along a longitudinal direction of the second jaw;
a fourth current supply portion projecting integrally from the second exothermic part on a distal end side of the second jaw;
a fifth current supply portion projecting integrally from the second exothermic part on a proximal end side of the second jaw;
a sixth current supply portion projecting integrally from the second exothermic part at a position between the fourth current supply portion and the fifth current supply portion; and
the controller connected to the fourth current supply portion, the fifth current supply portion and the sixth current supply portion, and configured to cause an electric current to flow, in the second exothermic part, between the fourth current supply portion and the fifth current supply portion, between the fourth current supply portion and the sixth current supply portion, or between the fifth current supply portion and the sixth current supply portion.

8. The thermocoagulation/cutting device of claim 7, wherein:
a dimension of a first portion of the exothermic part, which is located between the first current supply portion and the third current supply portion, with respect to a direction crossing a longitudinal direction of the exothermic part, is different from a dimension of a third portion of the second exothermic part, which is located between the fourth current supply portion and the sixth current supply portion and is opposed to the first portion, with respect to a direction crossing a longitudinal direction of the second exothermic part, and
a dimension of a second portion of the exothermic part, which is located between the second current supply portion and the third current supply portion, with respect to the direction crossing the longitudinal direction of the exothermic part, is different from a dimension of a fourth portion of the second exothermic part, which is located between the fifth current supply portion and the sixth current supply portion and is opposed to the second portion, with respect to the direction crossing the longitudinal direction of the second exothermic part.

* * * * *